(12) United States Patent
Liu et al.

(10) Patent No.: US 6,569,879 B2
(45) Date of Patent: May 27, 2003

(54) ARYLOXYACETIC ACIDS FOR DIABETES AND LIPID DISORDERS

(75) Inventors: Kun Liu, Edison, NJ (US); Libo Xu, Dayton, NJ (US); A. Brian Jones, Clavering (GB)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/932,834

(22) Filed: Aug. 17, 2001

(65) Prior Publication Data

US 2002/0173663 A1 Nov. 21, 2002

Related U.S. Application Data

(63) Continuation-in-part of application No. 09/782,856, filed on Feb. 14, 2001, now abandoned.
(60) Provisional application No. 60/183,593, filed on Feb. 18, 2000.

(51) Int. Cl.$^7$ .................... A61K 31/42; C07D 261/20; A61P 43/00
(52) U.S. Cl. .................. 514/373; 514/379; 548/207; 548/241
(58) Field of Search ................ 548/207, 241; 514/379, 373

(56) References Cited

U.S. PATENT DOCUMENTS

| 4,436,748 A | * | 3/1984 | Ong et al. |
| 4,528,399 A | * | 7/1985 | Ong et al. |
| 4,602,028 A | * | 7/1986 | Effland et al. |
| 4,663,347 A | * | 5/1987 | Atkinson et al. |
| 4,673,746 A | * | 6/1987 | Shutske et al. ............. 546/272 |
| 4,728,662 A | * | 3/1988 | Shutske et al. ............. 514/379 |
| 4,745,127 A | * | 5/1988 | Atkinson et al. |
| 5,599,821 A | * | 2/1997 | Glamkowski et al. |

FOREIGN PATENT DOCUMENTS

| WO | WO 99/58495 | * | 12/1999 |
| WO | WO 00/27199 | * | 5/2000 |
| WO | WO 00/27627 | * | 5/2000 |

OTHER PUBLICATIONS

Gregory M. Shutske, [(3–Aryl–1,2–benzisoxazol–6–yl)oxy] acetic Acids. A New Diuretic Series, Jun. 22, 1982, 36–44, vol. 25.

Gregory M. Shutske, Heterocyclic Oxyacetic Acid Diuretics: Indazole, Benzisothiazole, and Benzisothiazole 1,1–Dioxide Analogues of [[7–Chloro–3–(2–fluorophenyl)–122–benzisoxazole–6–yl] oxy]acetic Acid, Dec. 1, 1982, 1307–1311, vol. 26.

M. Kitzen, Characterization of the Renal Pharmacology of HP–522, A Loop Diuretic with Uricosuric Activity, 1980, 2547–2552, vol. 27.

* cited by examiner

*Primary Examiner*—Joseph K. McKanes
*Assistant Examiner*—Andrea D. Smith
(74) *Attorney, Agent, or Firm*—James L. McGinnis; Melvin Winokur

(57) ABSTRACT

A class of aryloxyacetic acids comprises compounds that are potent agonists of PPAR alpha and/or gamma, and are therefore useful in the treatment, control or prevention of non-insulin dependent diabetes mellitus (NIDDM), hyperglycemia, dyslipidemia, hyperlipidemia, hypercholesterolemia, hypertriglyceridemia, atherosclerosis, obesity, vascular restenosis, inflammation, and other PPAR alpha and/or gamma mediated diseases, disorders and conditions.

31 Claims, No Drawings

ARYLOXYACETIC ACIDS FOR DIABETES AND LIPID DISORDERS

CROSS-REFERENCE TO RELATED APPLICATIONS

This application is a Continuation-in-Part of U.S. application Ser. No. 09/782,856, filed Feb. 14, 2001, now abandonded, which claims priority from U.S. Provisional Application No. 60/183,593, filed Feb. 18, 2000.

FIELD OF THE INVENTION

The instant invention is concerned with aryloxyacetic acids and pharmaceutically acceptable salts and prodrugs thereof which are useful as therapeutic compounds, particularly in the treatment of Type 2 diabetes mellitus, often referred to as non-insulin dependent diabetes (NIDDM), of conditions that are often associated with this disease, and of lipid disorders.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide), which stimulate the pancreatic β-cells to secrete more insulin, and/or by injection of insulin after the response to sulfonylureas fails, will result in high enough insulin concentrations to stimulate the very insulin-resistant tissues. However, dangerously low levels of plasma glucose can result from these last two treatments, and increasing insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea, respectively.

The glitazones (i.e. 5-benzylthiazolidine-2,4-diones) are a more recently described class of compounds with potential for a novel mode of action in ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia.

Disorders of lipid metabolism or dyslipidemias include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL) . Cholesterol is mostly carried in Low Density Lipoproteins (LDL), and this component is commonly known as the "bad" cholesterol because it has been shown that elevations in LDL-cholesterol correlate closely to the risk of coronary heart disease. A smaller component of cholesterol is carried in the High Density Lipoproteins and is commonly known as the "good" cholesterol. In fact, it is known that the primary function of HDL is to accept cholesterol deposited in the arterial wall and to transport it back to the liver for disposal through the intestine. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707-714 (1977); Stampfer, et al., N. England J. Med., 325, 373-381 (1991); and Kannel, et al., Ann. Internal Med., 90, 85-91 (1979). An example of an HDL raising agent is nicotinic acid, a drug with limited utility because doses that achieve HDL raising are associated with undesirable effects, such as flushing.

Dyslipidemias were originally classified by Fredrickson according to the combination of alterations mentioned above. The Fredrickson classification includes 6 phenotypes (i.e., I, IIa, IIb, III, IV and V) with the most common being the isolated hypercholesterolemia (or type IIa) which is usually accompained by elevated concentrations of total and LDL cholesterol. The initial treatment for hypercholesterolemia is often to modify the diet to one low in fat and cholesterol, coupled with appropriate physical exercise, followed by drug therapy when LDL-lowering goals are not met by diet and exercise alone A second common form of dyslipidemia is the mixed or combined hyperlipidemia or type IIb and III of the Fredrickson classification. This dyslipidemia is often prevalent in patients with type 2 diabetes, obesity and the metabolic syndrome. In this dyslipidemia there are modest elevations of LDL-cholesterol, accompanied by more pronounced elevations of small dense LDL-cholesterol particles, VLDL and/or IDL (i.e., triglyceride rich lipoproteins), and total triglycerides. In addition, concentrations of HDL are often low.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of lipid modulating drugs, herbicides and phthalate plasticizers. Peroxisome proliferation is also triggered by dietary or physiological factors such as a high-fat diet and cold acclimatization.

Three sub-types of peroxisome proliferator activated receptor (PPAR) have been discovered and described; they are peroxisome proliferator activated receptor alpha (PPARα), peroxisome proliferator activated receptor gamma (PPARγ) and peroxisome proliferator activated receptor delta (PPARδ). Identification of PPARα, a member of the nuclear hormone receptor superfamily activated by peroxisome proliferators, has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also associated with the activity of fibrates and fatty acids in rodents and humans. Fibric acid derivatives such as clofibrate, fenofibrate, benzafibrate, ciprofibrate, beclofibrate and etofibrate, as well as gemfibrozil, each of which are PPARα ligands and/or activators, produce a substantial reduction in plasma triglycerides as well as some increase in HDL. The effects on LDL cholesterol are inconsistent and might depend upon the compound and/or the dyslipidemic phenotype. For these reasons, this class of compounds has been primarily used to treat hypertriglyceridemia (i.e, Fredrickson Type IV and V) and/or mixed hyperlipidemia.

The PPARγ receptor subtypes are involved in activating the program of adipocyte differentiation and are not involved in stimulating peroxisome proliferation in the liver. There are two known protein isoforms of PPARγ:PPARγ1 and PPARγ2 which differ only in that PPARγ2 contains an additional 28 amino acids present at the amino terminus. The DNA sequences for the human isotypes are described in Elbrecht, et al., BBRC 224;431-437 (1996). In mice, PPARγ2 is expressed specifically in fat cells. Tontonoz et al., *Cell* 79: 1147-1156 (1994) provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements, for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin $J_2$ derivatives have been identified as potential natural ligands of the PPARγ subtype, which also binds thiazolidinedione antidiabetic agents with high affinity.

The human nuclear receptor gene PPARδ (hPPARδ) has been cloned from a human osteosarcoma cell cDNA library and is fully described in A. Schmidt et al., *Molecular Endocrinology*, 6:1634-1641 (1992). It should be noted that PPARδ is also referred to in the literature as PPARβ and as NUC1, and each of these names refers to the same receptor; in Schmidt et al. the receptor is referred to as NUC 1.

In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARα and thyroid hormone receptor protein activity.

It has been disclosed in WO97/28149 that agonists of PPARδ are useful in raising HDL plasma levels. WO97/27857, 97/28115, 97/28137 and 97/27847 disclose compounds that are useful as antidiabetic, antiobesity, antiatherosclerosis and antihyperlipidemic agents, and which may exert their effect through activation of PPARs.

It is generally believed that glitazones exert their effects by binding to the peroxisome proliferator activated receptor (PPAR) family of receptors, controlling certain transcription elements having to do with the biological entities listed above. See Hulin et al., Current Pharm. Design (1996) 2, 85-102.

A number of glitazones that are PPAR agonists have been approved for use in the treatment of diabetes. These include troglitazone, rosiglitazone and pioglitazone, all of which are primarily or exclusively PPARγ agonists. Many of the newer PPAR agonists that are currently under development or are in clinical trials have dual PPARα and γ activity. These are expected to improve both insulin sensitivity and the lipid profile in patients having NIDDM.

Although glitazones are beneficial in the treatment of NIDDM, there have been some serious adverse events associated with the use of the compounds. The most serious of these has been liver toxicity, which has resulted in a number of deaths. The most serious problems have occurred using troglitazone. Because of the problems that have occurred with the glitazones, researchers in a number of laboratories have been investigating classes of PPAR agonists that are not glitazones and do not contain 1,3-thiazolidinedione moieties.

Compounds that are not glitazones but are agonists of PPAR sub-types are expected to be useful in the treatment of diabetes and associated conditions. PPARα agonists should improve the lipid profile and alleviate dyslipidemias by reducing elevated LDL levels and elevated triglyceride levels and/or increasing HDL levels. PPARγ agonists should improve insulin sensitivity, reducing the need for insulin injections in patients with NIDDM. The role of PPARδ is less well defined.

SUMMARY OF THE INVENTION

The class of compounds described herein is a new class of PPAR agonists that do not contain a 1,3-thiazolidinedione moiety and therefore are not glitazones. The class of compounds includes compounds that are primarily PPARα agonists and compounds that are mixed PPARα/γ agonists. These compounds are useful in the treatment, control and/or prevention of diabetes, hyperglycemia, mixed or diabetic dyslipidemia, and other lipid disorders (including isolated hypercholesterolemia as manifested by elevations in LDL-C and/or non-HDL-C and/or hyperapoBliproteinemia, hypertriglyceridemia and/or increase in triglyceride-rich-lipoproteins, or low HDL cholesterol concentrations), atherosclerosis, obesity, vascular restenosis, inflammatory conditions, neoplastic conditions, and other PPARα and/or γ mediated diseases, disorders and conditions.

The present invention provides compounds having the structure of Formula I, including pharmaceutically acceptable salts and prodrugs of these compounds:

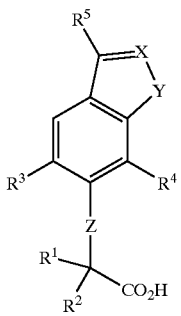

I

In the compounds of Formula I:

$R^1$ and $R^2$ are each independently selected from the group consisting of H, F, $C_{1-5}$ alkyl, $C_{2-5}$ alkenyl, and $C_{2-5}$ alkynyl, wherein said alkyl, alkenyl, and alkynyl may be linear or branched and are optionally substituted with 1-3 halogen atoms; or optionally $R^1$ and $R^2$ together form a $C_{3-6}$ cycloalkyl;

$R^3$ and $R^4$ are each independently selected from the group consisting of $C_1$–$C_5$ alkyl, $C_{2-5}$ alkenyl, $C_{2-5}$ alkynyl, and chlorine, provided that $R^3$ and $R^4$ are not both chlorine, wherein said alkyl, alkenyl, and alkynyl groups may be linear or branched and are optionally substituted with 1-5 fluorine atoms;

X is N or CR;

Y is O, S, or NR;

Z is O or S;

Each R group is selected from the group consisting of H, $C_{1-5}$ alkyl, $C_{2-5}$ alkenyl, and $C_{2-5}$ alkynyl, wherein said alkyl, alkenyl, and alkynyl may be linear or branched and are optionally substituted with 1-5 fluorine atoms and/or one —$OC_{1-3}$ alkyl, said —$OC_{1-3}$ alkyl being optionally substituted with 1-7 fluorine atoms; and $R^5$ is selected from the group consisting of H, $C_{1-6}$ alkyl, $C_{2-6}$ alkenyl, $C_{2-6}$ alkynyl, $C_{6-10}$ Aryl, —$OC_{1-6}$ alkyl, —$OC_{2-6}$ alkenyl, —$OC_{2-6}$ alkynyl, —$OC_{6-10}$ Aryl, $C_{3-6}$ Cycloalkyl, 5-6-membered Heterocyclyl, 5-6-membered Heteroaryl, —$OC_{3-6}$ Cycloalkyl, —O 5-6-membered Heterocyclyl, —O 5-6 membered Heteroaryl, and a $C_{1-4}$ alkyl group which comprises at a position interrupting the chain or at the end of the chain a group selected from $C_{6-10}$ Aryl, $C_{3-6}$ Cycloalkyl, 5-6-membered Heterocyclyl, and 5-6-membered Heteroaryl, wherein each of said alkyl, alkenyl, alkynyl, —Oalkyl, —Oalkenyl, and —Oalkynyl is linear or branched and is optionally substituted with 1-5 fluorine atoms and/or one —$OCH_3$ or —$OCF_3$ group, and each of said Aryl, Cycloalkyl, Heteroaryl, Heterocyclyl, —OAryl, —OCycloalkyl, —OHeteroaryl, and —OHeterocyclyl groups is optionally substituted with 1-7 halogen atoms and/or one —$OCH_3$ or —$OCF_3$ group.

These compounds are effective in lowering glucose, lipids, and insulin in diabetic animals. The compounds are expected to be efficacious in the treatment, control and/or prevention of non-insulin dependent diabetes mellitus (NIDDM) in humans and in the treatment, control, and/or prevention of conditions associated with NIDDM, including hyperlipidemia, dyslipidemia, obesity, hypercholesterolemia, hypertrigyceridemia, atherosclerosis, vascular restenosis, inflammatory conditions, neoplastic conditions, and other PPARα and/or γ mediated diseases, disorders and conditions.

DETAILED DESCRIPTION OF THE INVENTION

The invention has numerous embodiments. Several subsets of compounds having different heterocyclic rings are included, as follows:

Compounds of Formula I, in which X is N and Y is O;

Compounds of Formula I, in which X is N and Y is S;

Compounds of Formula I, in which X is N and Y is NR;

Compounds of Formula I, in which X is CR and Y is O;

Compounds of Formula I, in which X is CR and Y is S; and

Compounds of Formula I, in which X is CR and Y is NR.

In further subsets of the compounds of Formula I described above, in which the compounds of Formula I have different heterocycles fused to the aromatic ring (i.e. different values of X and Y), $R^5$ is selected from the group consisting of H, $C_{1-5}$ alkyl, $C_{2-5}$ alkenyl, $C_{2-5}$ alkynyl, $OC_{1-5}$ alkyl, $OC_{2-5}$ alkenyl, $OC_{2-5}$ alkynyl, and phenyl; in these compounds, the alkyl, alkenyl, alkynyl, —Oalkyl, —Oalkenyl, and —Oalkynyl are optionally substituted with 1-5 fluorine atoms, and phenyl is optionally substituted with 1-5 halogens. In a preferred subset, $R^5$ is selected from the group consisting of H, $C_{1-5}$ alkyl, $C_{2-5}$ alkenyl, $C_{2-5}$ alkynyl, $OC_{1-5}$ alkyl, $OC_{2-5}$ alkenyl, and $OC_{2-5}$ alkynyl, where alkyl, alkenyl, alkynyl, —Oalkyl, —Oalkenyl, and —Oalkynyl are optionally substituted with 1-5 fluorine atoms.

In preferred compounds, $R^1$ and $R^2$ are each H or $C_{1-3}$ alkyl, and the number of carbon atoms in $R^1$ and $R^2$ together is 0-5.

In preferred embodiments, $R^3$ and $R^4$ are each independently $C_{1-5}$ alkyl. In additional preferred embodiments, one of $R^3$ and $R^4$ is $C_{2-5}$ alkyl, and the other of $R^3$ and $R^4$ is $C_{1-5}$ alkyl. In another preferred embodiment, both $R^3$ and $R^4$ are $C_{2-5}$ alkyl. In other preferred compounds, one of $R^3$ and $R^4$ is Cl or $C_{1-5}$ alkyl, and the other of $R^3$ and $R^4$ is $C_{2-5}$ alkyl. In general, the alkyl groups are linear or branched. In the most preferred compounds $R^3$ and $R^4$ are linear when they are alkyl.

In preferred compounds, $R^5$ is selected from $C_{1-5}$ alkyl and —$OC_{1-5}$ alkyl, where the alkyl and —Oalkyl are optionally substituted with 1-5 fluorine atoms.

In preferred embodiments, Z is O.

In preferred embodiments, X is N and Y is O, so that the compounds are benzisoxazoles.

In highly preferred embodiments of the groups of compounds above, $R_5$ is $C_{1-3}$ alkyl, —$OC_{1-3}$ alkyl, $CF_3$, $C_2F_5$, —$OCF_3$ or —$OC_2F_5$; and $R^3$ and $R^4$ are each n-propyl Specific examples of compounds of this invention are provided as Examples 1-29.

The invention further includes pharmaceutical compositions comprising any of the compounds described above and a pharmaceutically acceptable carrier.

The compounds as defined above are useful in the following methods of treating, controlling, and preventing diseases, as well as other diseases not listed below:

(1) a method for treating, controlling or preventing diabetes mellitus, and particularly non-insulin dependent diabetes mellitus, in a mammalian patient in need of such treatment which comprises administering to the patient a therapeutically effective amount of a compound of Formula I;

(2) a method for treating, controlling, or preventing hyperglycemia in a mammalian patient in need of such treatment which comprises administering to the patient a therapeutically effective amount of a compound of Formula I;

(3) a method for treating, controlling, or preventing lipid disorders, hyperlipidemia, or low HDL in a mammalian patient in need of such treatment which comprises administering to the patient a therapeutically effective amount of a compound of Formula I;

(4) a method for treating, controlling, or preventing obesity in a mammalian patient in need of such treatment which comprises administering to the patient a therapeutically effective amount of a compound of Formula I;

(5) a method for treating, controlling, or preventing hypercholesterolemia in a mammalian patient in need of such treatment which comprises administering to the patient a therapeutically effective amount of a compound of Formula I;

(6) a method for treating, controlling, or preventing hypertriglyceridemia in a mammalian patient in need of such treatment which comprises administering to the patient a therapeutically effective amount of a compound of Formula I;

(7) a method for treating, controlling, or preventing dyslipidemia, including low HDL cholesterol, in a mammalian patient in need of such treatment which comprises administering to the patient a therapeutically effective amount of a compound of Formula I;

(8) a method for treating, controlling, or preventing atherosclerosis in a mammalian patient in need of such treatment which comprises administering to the patient a therapeutically effective amount of a compound of Formula I. It is understood that the sequellae of atherosclerosis (angina, claudication, heart attack, stroke, etc.) are thereby treated.

DEFINITIONS

"Ac" is acetyl, which is $CH_3C(O)$—.

"Alkyl", as well as other groups having the prefix "alk", such as alkoxy or alkanoyl, means carbon chains which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon—carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon–carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each having from 3 to 10 carbon atoms. The term also includes a monocyclic ring fused to an aryl group in which the point of attachment is on the non-aromatic portion. Examples of cycloalkyl include cyclopropyl, cyclopentyl, cyclohexyl, cycloheptyl, and the like.

"Aryl" (and "arylene") means mono- or bicyclic aromatic rings containing only carbon ring atoms. The term also includes an aryl group fused to a monocyclic cycloalkyl or monocyclic heterocyclic group in which the point(s) of attachment is on the aromatic portion. The preferred aryl is phenyl. "Heterocycle" and "heterocyclic" means a fully or partially saturated monocyclic, bicyclic or tricyclic ring containing at least one heteroatom selected from N, S and O, each of said rings having from 3 to 10 atoms. Examples of aryl include phenyl, naphthyl, indanyl, indenyl, and tetrahydronaphthyl. Examples of aryl fused to heterocyclic groups include 2,3-dihydrobenzofuranyl, benzopyranyl, 1,4-benzodioxanyl, and the like. Examples of heterocycles include tetrahydrofuran, piperazine, and morpholine.

"Heteroaryl" (and heteroarylene) means a mono-, bi- or tricyclic aromatic ring containing at least one ring heteroatom selected from N, O and S (including SO and $SO_2$), with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, dibenzofuran and the like.

"Halogen" includes fluorine, chlorine, bromine and iodine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers—Diastereomers—Geometric Isomers—Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form, known as keto-enol tautomers. The individual tautomers as well as mixtures thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid or base as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Metabolites of the compounds of this invention that are therapeutically active also are within the scope of the claimed parent compound. Prodrugs, which are compounds that are converted to the claimed compounds as they are being administered to a patient or after they have been administered to a patient, are also within the scope of the claimed active compound. A non-limiting example of a prodrug of the carboxylic acids of this invention would be an ester of the carboxylic acid group, for example a $C_1$ to $C_6$ ester, which may be linear or branched, or an ester which has functionality that makes it more easily hydrolyzed after administration to a patient.

Prodrugs of this class of compounds may be described as compounds having the Formula Ia:

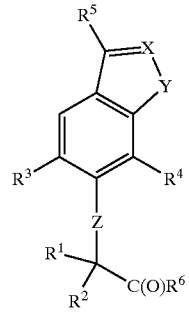

Ia wherein $R^6$ is a group that is easily removed under physiological conditions during or after administration to a mammalian patient to yield a compound having Formula I, or the carboxylate anion thereof (in solution), or a pharmaceutically acceptable salt thereof, where $R^1$, $R^2$, $R^3$, $R^4$, $R^5$, X, Y, Z, and R are as defined above for compounds having Formula I.

Examples of prodrugs of Formula Ia include compounds in which $R^6$ is selected from the group consisting of —$OR^7$, —$OCH_2OR^7$, —$OCH(CH_3)OR^7$, —$OCH_2OC(O)R^7$, —$OCH(CH_3)OC(O)R^7$, —$OCH_2OC(O)OR^7$, —$OCH(CH_3)OC(O)OR^7$, —$NR^8R^8$, and —$ONR^8R^8$, where each $R^7$ is independently selected from $C_{1-6}$ alkyl optionally substituted with one or two groups selected from —$CO_2H$, —$CONH_2$, —$NH_2$, —OH, —OAc, NHAc, and phenyl; and wherein each $R^8$ is independently selected from H and $R^7$. Compounds having Formula Ia, where $R_6$ has the chemical structure described above, are described as prodrugs. However, regardless of whether they are active as prodrugs, yielding compounds or salts of Formula I, or whether they have a different means of exhibiting pharmaceutical activity, the compounds of Formula Ia are included in this invention. Such compounds are claimed herein, regardless of the mechanism leading to their activity.

The description of utility, pharmaceutical compositions, combination therapies, administration, dosage, and the like are all described in terms of compounds of Formula I. These descriptions of utility, etc. also apply to compounds of Formula Ia.

Utilities

Compounds of the present invention are potent agonists of varioius peroxisome proliferator activator receptor subtypes, particularly PPARα and/or PPARγ. Compounds of the present invention may be selective agonists of one receptor subtype, e.g. PPARγ or PPARα agonists, or they may be agonists of more than one receptor subtypes, e.g. dual PPARα/γ agonists. Compounds of the present invention are useful in treating, controlling or preventing diseases, disorders or conditions, wherein the treatment is mediated by the activation of an individual PPAR subtype (α or γ), or a combination of PPAR subtypes (e.g. α/γ). Thus one aspect of the present invention provides a method for the treatment, control or prevention of such diseases, disorders, or conditions in a mammal which comprises administering to such mammal a therapeutically effective amount of a compound of Formula I. The diseases, disorders or conditions for which compounds of the present invention are useful in treating, controlling or preventing include, but are not limited to, (1)

diabetes mellitus, and especially non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29)high blood pressure, (30) Syndrome X, (31) ovarian hyperandrogenism (polycystic ovarian syndrome), and other disorders where insulin resistance is a component.

Another aspect of the invention provides a method for the treatment, control, or prevention of hypercholesterolemia, atherosclerosis, low HDL levels, high LDL levels, hyperlipidemia, hypertriglyceridemia, and/or dyslipidemia, which comprises administering to a mammal in need of such treatment a therapeutically effective amount of an agonist of PPARα and/or PPARγ or a PPARα/γ dual agonist. The PPAR agonist may be used alone or advantageously may be administered with a cholesterol biosynthesis inhibitor, particularly an HMG-CoA reductase inhibitor such as lovastatin, simvastatin, pravastatin, fluvastatin, atorvastatin, rivastatin, itavastatin, or ZD-4522. The PPAR agonist may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), and with niacin, bile acid sequestrants, microsomal triglyceride transport inhibitors, and bile acid reuptake inhibitors. These combination treatments may also be effective for the treatment, control or prevention of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a PPAR agonist, which may be a PPARα agonist, a PPARγ agonist, or a PPARα/γ dual agonist. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment, prevention, suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin; (iii) protein tyrosine phosphatase-1B (PTP-1B) inhibitors, and (iv) dipeptidyl peptidase IV (DP-IV) inhibitors;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin, pravastatin, fluvastatin, atorvastatin, rivastatin, itavastatin, ZD-4522 and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) PPARα/γ dual agonists, such as KRP-297, (vi) inhibitors of cholesterol absorption, such as for example beta-sitosterol, (vii) acyl CoA:cholesterol acyltransferase inhibitors, such as for example avasimibe, and (viii) anti-oxidants, such as probucol;

(f) PPARδ agonists such as those disclosed in WO97/28149;

(g) antiobesity compounds such as fenfluramine, dexfenfluramine, phentiramine, sulbitramine, orlistat, neuropeptide Y5 inhibitors, and $β_3$ adrenergic receptor agonists;

(h) an ileal bile acid transporter inhibitor; and (i) agents intended for use in inflammatory conditions such as aspirin, non-steroidal anti-inflammatory drugs, glucocorticoids, azulfidine, and cyclooxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

BIOLOGICAL ASSAYS

A) PPAR Binding Assays

For preparation of recombinant human PPARγ, PPARδ, and PPARα: Human $PPARγ_2$, human PPARδ and human PPARα were expressed as gst-fusion proteins in *E. coli*. The full length human cDNA for $PPARγ_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C. For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$] AD5075, (21 Ci/mmole), ± test compound as described in Berger et al (Novel peroxisome proliferator-activated receptor (PPARγ) and PPARδ ligands produce distinct biological effects. J. Biol. Chem. (1999), 274: 6718-6725. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]-Comp'd A, (17 Ci/mmole), ± test compound as described in Berger et al (Novel peroxisome proliferator-activated receptory (PPARγ) and PPARδ ligands produce distinct biological effects.1999 J Biol Chem 274: 6718-6725). (Comp'd A is 3-chloro-4-(3-(7-propyl-3-trifluoromethyl-6-benz-[4,5]-isoxazoloxy)prophylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$]-Comp'd B, (34 Ci/mmole), ± test compound. (Comp'd B is (3-(4-(3-phenyl-7-propyl-6-benz-[4,5]-isoxazoloxy)butyloxy))phenylacetic acid, Ex.62 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B). Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5x)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37 ° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5x)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate ± increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

C. In Vivo Studies

Male db/db mice (10-11 week old C57B1/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose) ± test compound at the indicated dose. Drug suspensions were prepared daily. Plasma glucose, and triglyceride concentrations were determined from blood obtained by tail bleeds at 3-5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

EXAMPLES

The following Examples are provided only to illustrate the invention, including methods of making the compounds of the invention, and are not to be construed as limiting the invention in any manner.

INTERMEDIATE 1

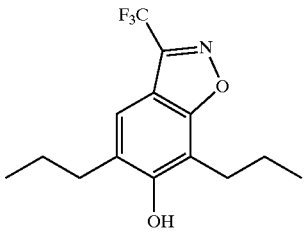

Step 1. Preparation of 1,3-diallyloxybenzene:

To a solution of resorcinol (1,200 g, 10.9 mmol) in DMF (10.89 L) was added K$_2$CO$_3$ (4,463 g). Allyl bromide (3,811 mL) was added slowly (keeping the temperature below 30°

C.). The reaction mixture was stirred at ambient temperature overnight, poured into water (94 L), extracted with Et$_2$O (3×20L). Combined organic layers were washed with water (3×15 L) and brine (10 L), dried over MgSO$_4$, filtered through Na$_2$SO$_4$, and evaporated in vacuo. The residue was pumped dry on high vacuum to give the crude product as a red/yellow oil, which was used in the next step without further purification. $^1$H NMR (CDCl$_3$, 400 MHz) δ 4.5 (d, 4H), 5.27 (m, 2H), 5.42 (m, 2H), 6.05 (m, 2H), 6.5 (m, 3H), 7.16 (m, 1H).

Step 2. Preparation of 2,4-diallylresorcinol:

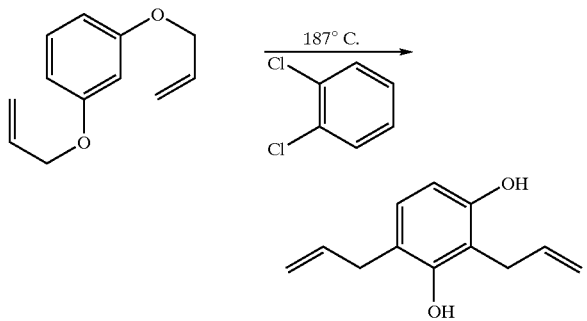

The crude starting material (2,278 g) was dissolved in 1,2-dichlorobenzene (11.4 L) in a 22 L 4-neck flask equipped with a mechanical stirrer, a thermocouple, a distillation condenser and a nitrogen inlet. A portion of the solvent (1.7 L) was distilled off at 187° C. before the distillation condenser was switched to a reflux condenser. The reaction was refluxed at 187° C. overnight. Ice-water (4 L) was added, followed by NaOH (320 g). The mixture was poured into hexanes (12 L) and layers were separated. The organic layer was extracted with aqueous NaOH (2 N, 2×4 L). The combined aqueous layers were acidified with concentrated HCl (ice was added to maintain the temperature below 30° C.), then extracted with Et$_2$O (3×4 L). The combined organic layers were dried over MgSO$_4$, filtered through Na$_2$SO$_4$, and evaporated in vacuo. Purification by chromatography (12 kg silica gel packed in hexanes, eluted with 10% EtOAc/hexanes) to give the desired product. $^1$H NMR (CDCl$_3$, 400 MHz) δ 3.31 (m, 2H), 3.48 (m, 2H), 5.2 (m, 4H), 6.0 (m, 2H), 6.40 (d, 1H), 6.85 (d, 1H).

Step 3. Preparation of 2,4-dipropylresorcinol:

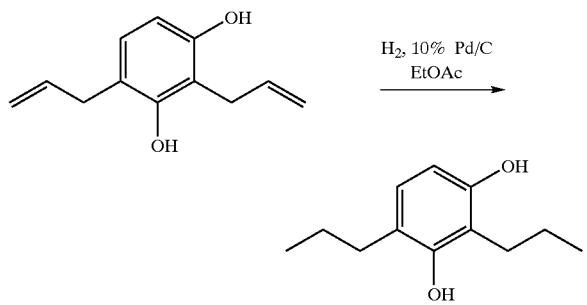

Starting material (1237.2 g, 6.5 mmol) was split into two runs. To each solution of the bis-allyl starting material (618.6 g) in ethyl acetate (2,780 mL) was added 10% Pd/C (46 g). Hydrogenation was carried out at rt under 40 psi hydrogen atmosphere for 1.5 h. The reaction was filtered through super cell, and the solvent was evaporated in vacuo. The combined crude products from the two runs were slurried in hexanes, filtered, and dried to give the product.

$^1$H NMR (CDCl$_3$, 400 MHz) δ 1.00 (m, overlapping signals, 6H), 1.6 (m, overlapping signals, 4H), 2.48 (t, 2H), 2.60 (t, 2H), 4.56 (s, 1H), 4.70 (s, 1H), 6.31 (d, 1H), 6.80 (d, 1H).

Step 4. Preparation of 2,4-dihydroxy-3,5-dipropyl-1', 1', 1'-trifluoroacetonephenone:

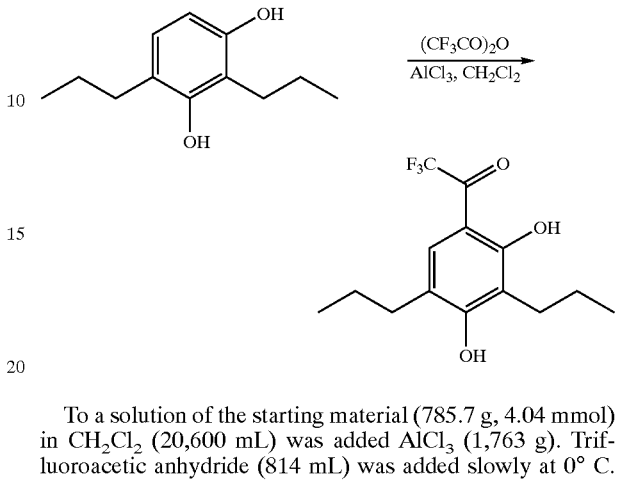

To a solution of the starting material (785.7 g, 4.04 mmol) in CH$_2$Cl$_2$ (20,600 mL) was added AlCl$_3$ (1,763 g). Trifluoroacetic anhydride (814 mL) was added slowly at 0° C. The reaction mixture was stirred overnight at rt, poured into ice-water, extracted with CH$_2$Cl$_2$ (3×). The combined organic layers were washed with sat. NaHCO$_3$ and brine, dried over MgSO$_4$, filtered through Na$_2$SO$_4$, and evaporated in vacuo. Purification by chromatography (10 kg silica gel, packed in hexanes, eluted with 5% EtOAc/hexanes) to give the desired product as a yellow solid. $^1$H NMR (CDCl$_3$, 400 MHz) δ 1.00 (m, overlapping signals, 6H), 1.60 (m, overlapping signals, 4H), 2.55 (t, J=7.4 Hz, 2H), 2.66 (t, J=7.4 Hz, 2H), 5.65 (s, 1H), 7.45 (s, 1H); MS (ESI) 291 (M+1).

Step 5. Preparation of 2,4-dihydroxy-3,5-dipropyl-1', 1', 1'-trifluoroacetonephenone oxime:

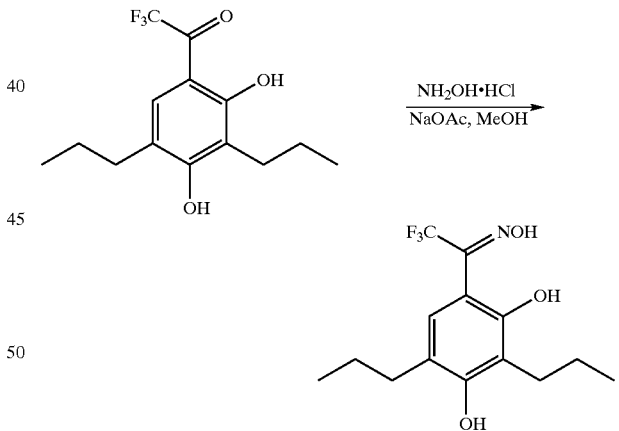

To a mixture of NaOAc (2,677 g, 32.5 mol) and hydroxyamine hydrochloride (2,000 g, 28.8 mol) in methanol (1 L) was added a solution of the starting phenol (1,139.8 g, 3.93 mol) in methanol (26 L). The yellow suspension was refluxed for 18 h. TLC showed significant amount of starting material remained. Additional hydroxyamine hydrochloride (1,000 g), NaOAc (1,338 g) and methanol (4 L) were added. The reaction mixture was refluxed overnight. TLC indicated the complete consumption of the starting material. The reaction was poured into ice-water (32 L), extracted with EtOAc (2×16 L). The combined organic layers were washed with brine, dried, and evaporated in vacuo. Chromatography (10 kg silica gel, 15% EtOAc/hexanes) gave the desired product as yellow solid. $^1$H NMR (CDCl$_3$, 400 MHz) δ 0.98 (m, overlapping signals, 6H), 1.60 (m, overlapping signals, 4H), 2.50 (t, 2H), 2.68 (t, 2H), 5.00 (s, broad, 1H), 5.80 (s, broad, 1H), 6.92 (s, 1H).

Step 6. Preparation of 5,7-dipropyl-6-hydroxy-3-trifluoromethyl-1,2-benzisoxazole:

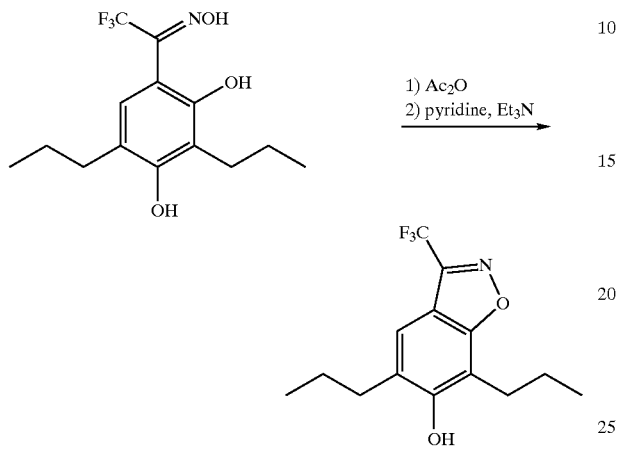

A solution of the starting oxime (600 g) in Ac$_2$O (3 L) was stirred at rt overnight. The solvent was removed in vacuo. The residue was coevaporated with toluene (4×) to give the crude 2,4-dihydroxy-3,5-dipropyl-1', 1', 1'-trifluoroacetonephenone O-acetyl oxime. This crude product was dissolved in pyridine (6 L) and Et$_3$N (684 mL). The reaction was refluxed (112° C.) for 3 h, and allowed to cool overnight. The solvent was evaporated in vacuo. The residue was coevaporated with toluene (2×), then partitioned between EtOAc and 1 N HCl. The organic layer was washed with 1 N HCl and brine, dried, filtered, and concentrated in vacuo to give a black oil. Purification by flash chromatography (10 kg silica gel, 5% EtOAc/hexanes) gave the desired product. $^1$H NMR (CDCl$_3$, 400 MHz) δ 1.00 (m, overlapping signals, 6H), 1.70 (m, overlapping signals, 4H), 2.68 (t, 2H), 2.90 (t, 2H), 5.21 (s, 1H), 7.33 (s, 1H); MS (ESI) 288.3 (M+1).

INTERMEDIATE 2

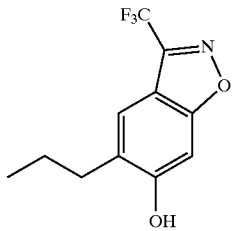

Similarly prepared as Intermediate 1 using 6-propylresorcinol. $^1$H NMR (CDCl$_3$, 400 MHz) δ 1.03 (t, 3H), 1.71 (m, 2H), 2.72 (t, 2H), 5.5 (s, broad, 1H), 7.06 (s, 1H), 7.51 (s, 1H).

INTERMEDIATE 3

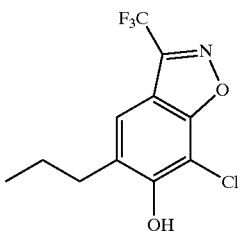

To a solution of Intermediate 2 (0.22 g, 0.89 mmol) and sulfuryl chloride (0.096 mL, 1.2 mmol) in CH$_2$Cl$_2$ (5 mL) was adde Et$_2$O (0.5 mL). The reaction was stirred at room temperature overnight, partitioned between water and Et$_2$O. The organic layer was washed with saturated NaHCO$_3$ aqueous solution and brine, dried over MgSO$_4$, filtered and concentrated in vacuo to give 7-chloro-6-hydroxy-5-propyl-3-trifluoromethyl-1,2-benzisoxazole. $^1$H NMR (CDCl$_3$, 400 MHz) δ 1.01 (t, 3H), 1.71 (m, 2H), 2.77 (t, 2H), 6.15 (s, 1H), 7.44 (s, 1H).

EXAMPLE 1

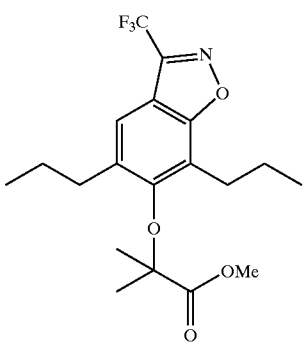

Preparation of methyl 2-[(5,7-dipropyl-3-trifluoromethyl-1,2-benzisoxazol-6-yl)oxy]-2-methylpropionate:

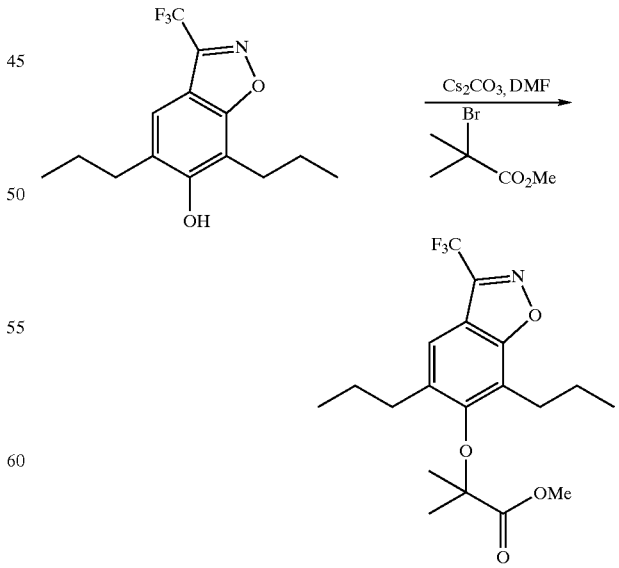

To a solution of starting phenol (20 g, 69.7 mmol) in DMF (200 ML) were added methyl α-bromoisobutyrate (126.7 g, 0.7 mol) and cesium carbonate (228 g, 0.7 mol) and the mixture was stirred at 60° C. for seven days. Reaction was worked up by partitioning between ether and water. The aqueous phase was extracted with ether and the organic phase was washed with water, then brine, dried over $Mg_2SO_4$, filtered, and evaporated in vacuo. Purification by chromatography gave the desired product. $^1$H NMR (CDCl$_3$): δ 1.00 (m, 6H), 1.53 (s, 6H), 1.69 (m, 2H), 1.76 (m, 2H), 2.62 (t, 2H), 2.85 (m, 2H), 3.89 (s, 3H), 7.39 (s, 1H).

EXAMPLE 2

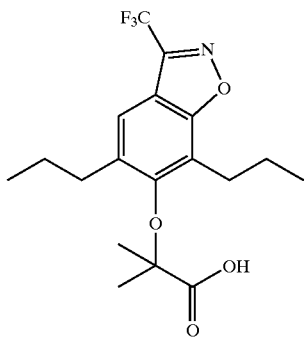

Preparation of 2-[(5,7-dipropyl-3-trifluoromethyl-1,2-benzisoxazol-6-yl)oxy]-2-methylpropionic acid:

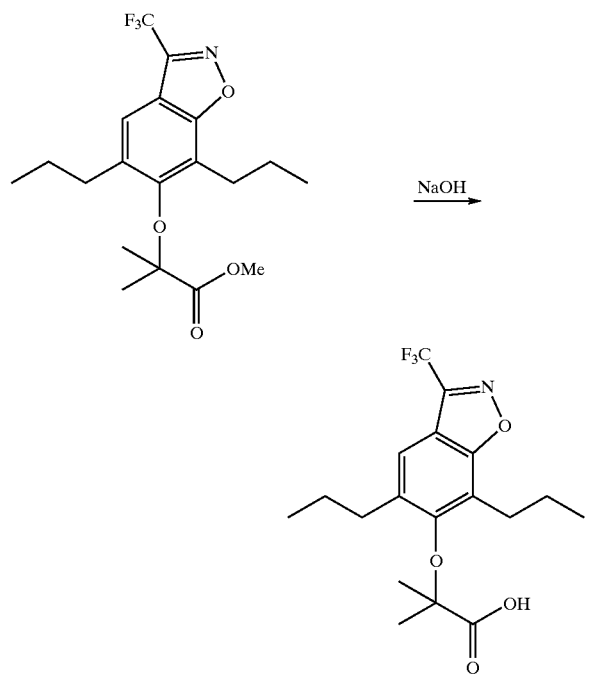

To a solution of the starting methyl ester (8 g, 20.7 mmol) in methanol (50 mL) was added aqueous sodium hydroxide (1.0 N, 60 mL). Enough THF (100 mL) was added to bring the mixture back to a clear solution. The mixture was heated at 80 ° C. for 2 h. TLC showed that reaction was complete. The reaction was partitioned between 1N HCl and ether. The organic phase was washed with water and brine, dried over magnesium sulfate, filtered, and evaporated in vacuo. The solid residue was recrystallized from pentane to afford the desired product as colorless crystals. $^1$H NMR (CDCl$_3$): δ 1.01 (m, 6H), 1.59 (s, 6H), 1.70 (m, 2H), 1.78 (m, 2H), 2.68 (t, 2H), 2.92 (m, 2H), 7.43 (s, 1H).

EXAMPLE 3

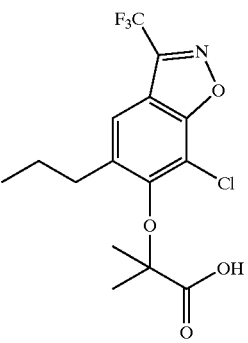

Similarly prepared as Example 2 using Intermediate 3. $^1$H NMR (CDCl$_3$, 400 MHz) δ 1.03 (t, 3H), 1.68 (s, 6H), 1.72 (m, 2H), 2.75 (t, 2H), 7.52 (s, 1H).

EXAMPLE 4

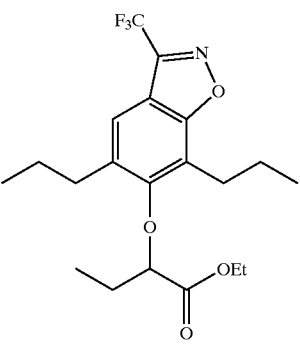

Preparation of ethyl 2-[(5,7-dipropyl-3-trifluoromethyl-1,2-benzisoxazol-6-yl)oxy]butyrate:

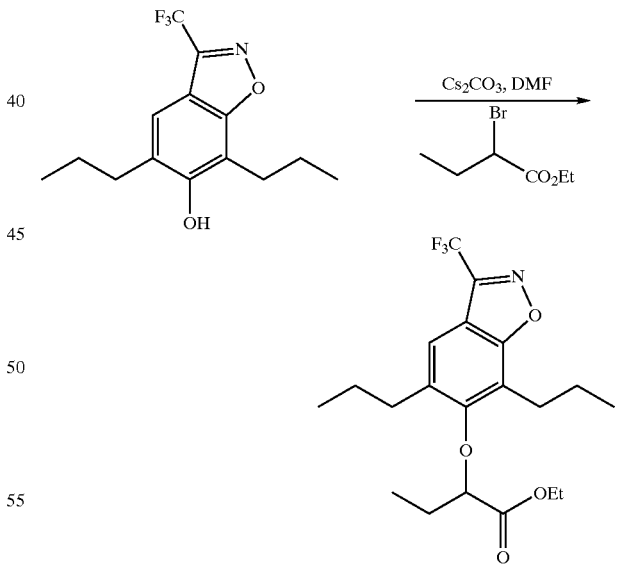

To a solution of Intermediate 1 (150 mg, 0.52 mmol) and ethyl 2-bromobutyrate (152 mg, 0.78 mmol) in DMF (5 mL) was added cesium carbonate (254 mg, 0.78 mmol). The mixture was stirred at room temperature for 6 h, then partitioned between ether and water. The organic phase was washed with water and brine, dried over magnesium sulfate, filtered, and concentrated in vacuo. Purification by flash chromatography gave the desired product. $^1$H NMR (CDCl$_3$): δ 1.01 (m, 6H), 1.08 (t, 3H), 1.24 (t, 3H), 1.69 (m, 2H), 1.78 (m, 2H), 2.04 (m, 2H), 2.72 (m, 1H), 2.82 (m, 1H), 2.97 (m, 2H), 4.19 (m, 2H), 4.54 (m, 1H), 7.41 (s, 1H).

EXAMPLE 5

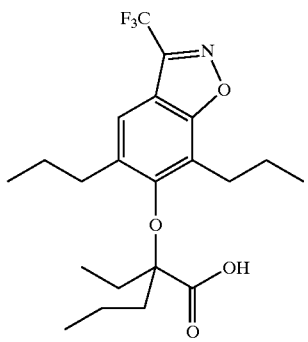

Step 1. Preparation of ethyl 2-[(5,7-dipropyl-3-trifluoromethyl-1,2-benzisoxazol-6-yl)oxy]-2-ethylvalerate:

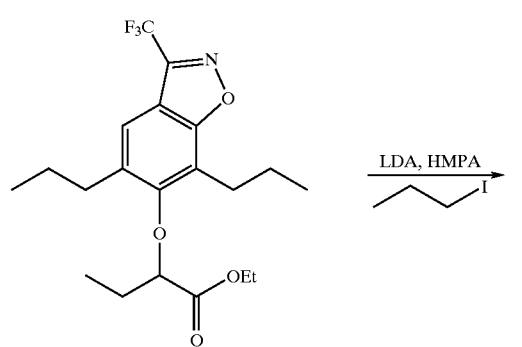

To a solution of the title compound of Example 5 (80 mg) in THF (5 mL) at −78° C. was added LDA (1.5 M, 0.27 mL) followed by HMPA (0.069 mL). After 5 min at −78° C., iodopropane (98 μL) was introduced. The mixture was stirred at −78° C. for 1 h, then allowed to slowly warm to room temperature over 2 h. Aqueous workup and purification by chromatography gave the desired product as a colorless oil. $^1$H NMR(CDCl$_3$): δ 0.87 (t, 3H), 0.95 (t, 3H), 1.01 (m, overlapping signals, 6H), 1.25 (m, 1), 1.50-1.80 (m, overlapping signals, 5H), 1.82-2.10 (m, overlapping signals, 4H), 2.68 (m, 2H), 2.91 (m, 2H), 4.18 (q, 2H), 7.38 (s, 1H).

Step 2. Preparation of 2-[(5,7-dipropyl-3-trifluoromethyl-1,2-benzisoxazol-6-yl)oxy]-2-ethylvaleric acid:

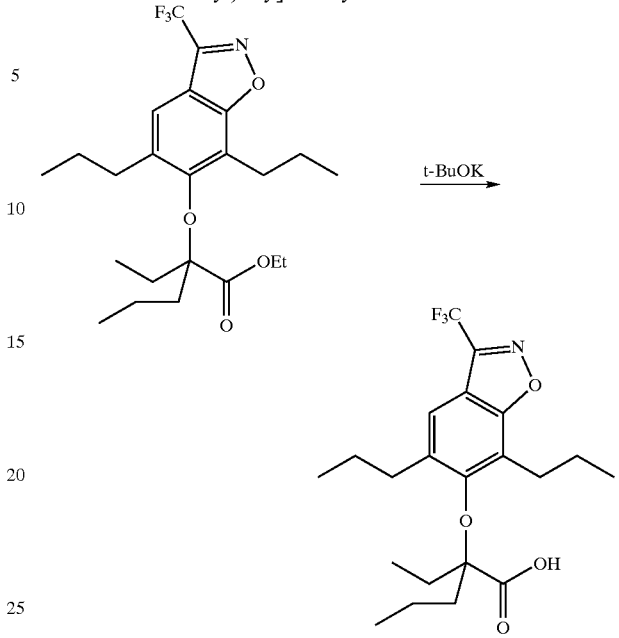

To a solution of the ethyl ester (30 mg) in DMSO (5 mL) at room temperature was added tBuOK (0.5 g). The reaction was stirred at room temperature overnight, partitioned between 1.0 N aqueous HCl and EtOAc. The organic phase was washed with water and brine, dried over magnesium sulfate, filtered, and concentrated in vacuo. Purification by preparative HPLC gave the desired product. $^1$H NMR (CDCl$_3$) δ 0.87 (t, 3H), 0.95 (t, 3H), 1.01 (m, 6H), 1.25 (m, 1H), 1.56-1.77 (m, 5H), 1.82 -2.10 (m, 4H), 2.69 (m, 2H), 2.91 (m, 2H), 7.42 (s, 1H).

EXAMPLE 6

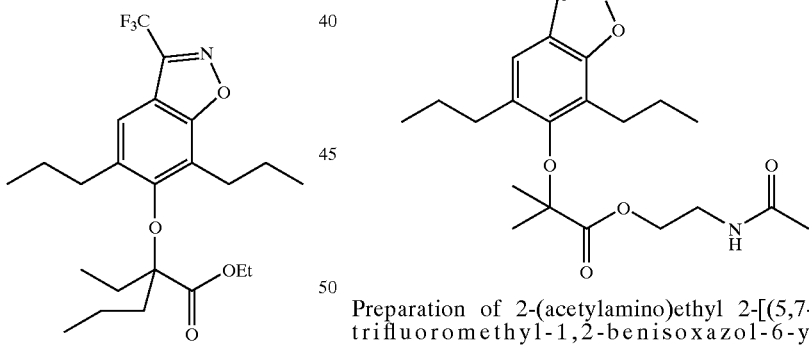

Preparation of 2-(acetylamino)ethyl 2-[(5,7-dipropyl-trifluoromethyl-1,2-benisoxazol-6-yl)oxy]-2-methylpropionate:

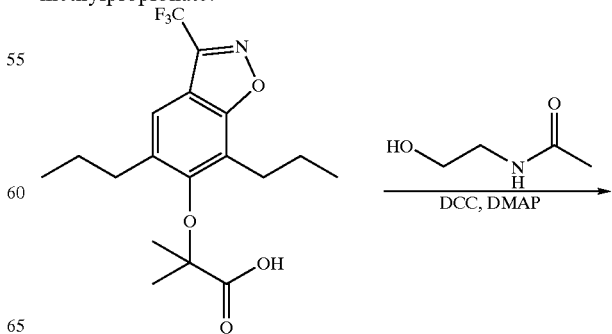

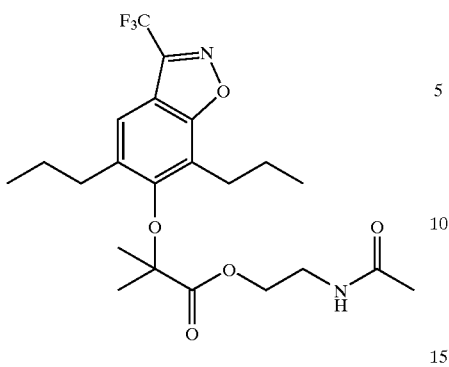

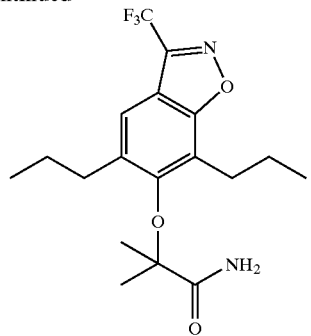

To a solution of the title compound of Example 1 (500 mg, 1.34 mmol) in methylene chloride (10 mL) were added N-2-hydroxyethylacetamide (166 mg, 1.50 mmol), DCC (1.5 mL, 1N) and DMAP (16 mg, 0.13 mmol). The reaction was stirred at room temperature overnight. Precipitates were filtered off. Filtrate and washings were combined and evaporated in vacuo. Purification by flash chromatography gave the desired product. $^1$H NMR (CDCl$_3$) δ 1.00 (m, 6H), 1.54 (s, 6H), 1.59-1.81 (m, 4H), 2.02 (s, 3H), 2.62 (t, 2H), 2.87 (m, 2H), 3.65 (m, 2H), 4.34 (t, 3H), 5.79 (s, broad, 1H), 7.40 (s, 1H).

EXAMPLE 7

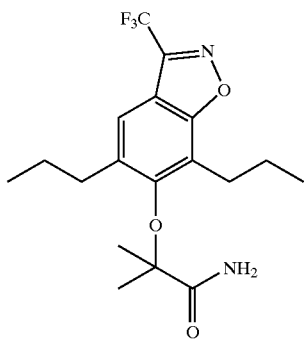

Preparation of 2-[(5,7-dipropyl-3-trifluoromethyl-1,2-benzisoxazol-6-yl)oxy]-2-methylpropionamide:

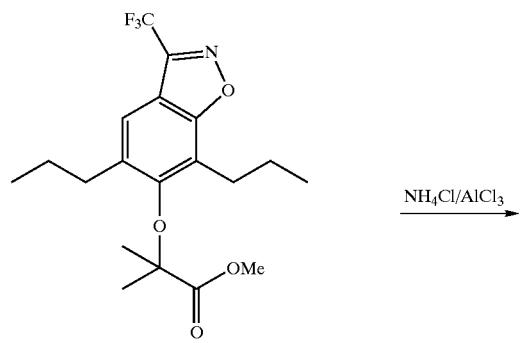

To a suspension of NH4Cl (86 mg) in toluene (10 mL) at room temperature was added AlCl3 (2.0 M, 0.8 mL) dropwise. The reaction was stirred for 3 h. The resultant clear solution was transferred to a solution of methyl 2-[(5,7-dipropyl-3-trifluoromethyl-1,2-benzisoxazol-6-yl)oxy]-2-methylpropionate (200 mg) in toluene (5 mL). The reaction was stirred at 80° C. overnight, cooled to room temperature, and then partitioned between EtOAc and 1.0 N aqueous HCl solution. The organic phase was washed with water and brine, dried over magnesium sulfate, filtered, and concentrated in vacuo. Purification by chromatography gave the desired product. $^1$H NMR (CDCl$_3$) δ 1.00 (m, 6H), 1.51 (s, 6H), 1.65 (m, 2H), 1.75 (m, 2H), 2.70 (t, 2H), 2.94 (m, 2H), 5.72 (s, broad, 1H), 6.87 (s, broad, 1H), 7.43 (s, 1H).

EXAMPLE 8

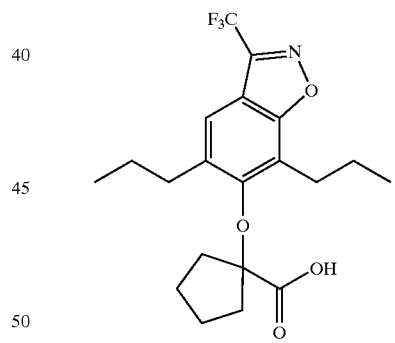

Step 1. Preparation of methyl [(5,7-dipropyl-3-trifluoromethyl-1,2-benzisoxazol-6-yl)oxy]acetate:

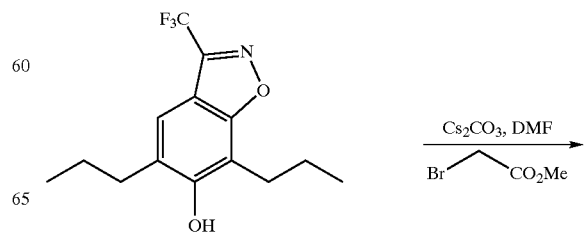

-continued

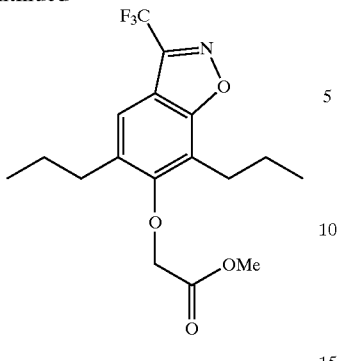

To a solution of starting phenol (0.5 g) in DMF (10 mL) were added methyl bromoacetate (0.4) and cesium carbonate (0.85) and the mixture was stirred at rt for 4 h. Reaction was worked up by partitioning between EtOAc and water. The organic phase was washed with water, then brine, dried over $Mg_2SO_4$, filtered, and evaporated in vacuo. Purification by chromatography gave the desired product. $^1$H NMR (CDCl$_3$): δ 1.02 (m, 6H), 1.72 (m, 2H), 1.80 (m, 2H), 2.74 (t, 2H), 2.97 (m, 2H), 3.89 (s, 3H), 4.51 (s, 2H), 7.45 (s, 1H).

Step 2. Preparation of methyl 1-[(5,7-dipropyl-3-trifluoromethyl-1,2-benzisoxazol-6-yl)oxy]cyclopentanecarboxylate:

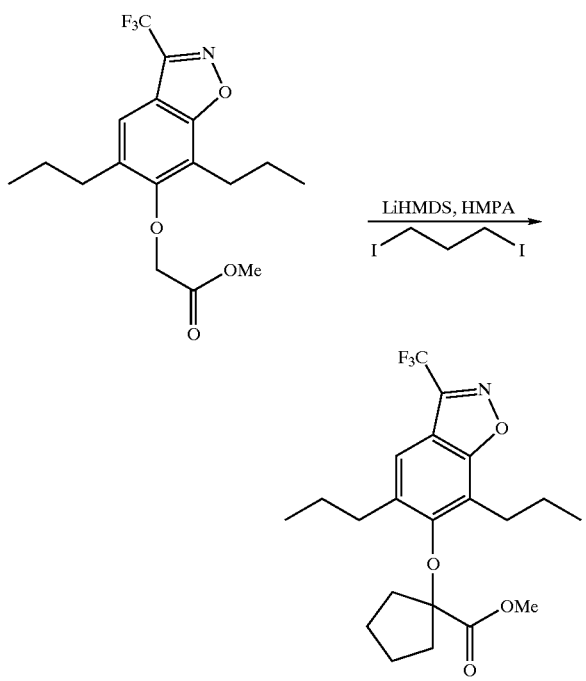

To a solution of the starting ester (100 mg) in THF (4.0 mL) at −78° C. were added LiHMDS (1.0 M, 0.31 mL) and HMPA (0.054 mL). After 15 min at −78 ° C., 1,4-diiodobutane (96 mg) was introduced. The reaction was allowed to warm to rt over 3 h, then cooled to −78° C. before another 2.1 equiv of LiHMNDS and HMPA were added. The reaction was allowed to slowly warm to rt and stirred overnight. The mixture was then partitioned between EtOAc and water. The organic phase was washed with water and brine, dried over magnesium sulfate, filtered, and concentrated in vacuo. Purification by chromatography gave the desired product. $^1$H NMR (CDCl$_3$) δ 0.99 (m, 6H), 1.72 (m, 8H), 2.08 (m, 2H), 2.32 (m,2H), 2.63 (t, 2H), 2.84 (t, 2H), 3.81 (s, 3H), 7.39 (s, 1H).

Step 3. Preparation of 1-[(5,7-dipropyl-3-trifluoromethyl-1,2-benzisoxazol-6-yl)oxy]cyclopentanecarboxylic acid:

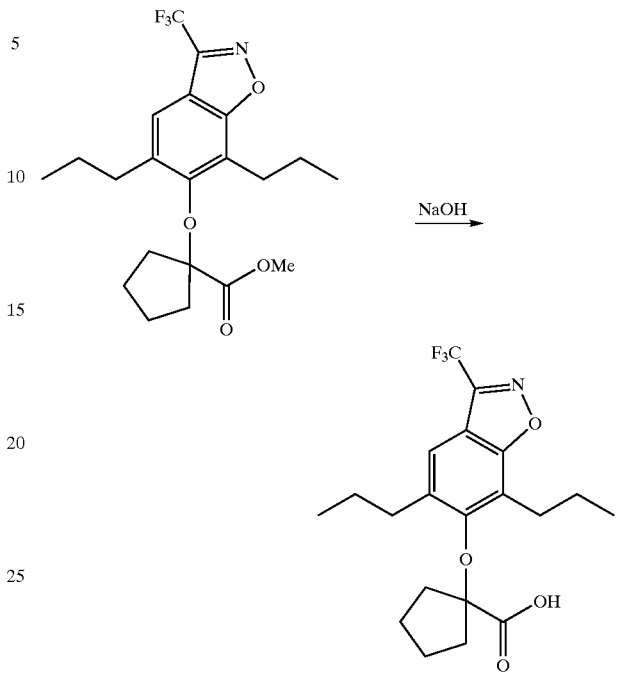

To a solution of the starting methyl ester (30 mg) in methanol (2 mL) was added aqueous sodium hydroxide (1.0 N, 2 mL). Enough THF (6 mL) was added to bring the mixture back to a clear solution. The mixture was heated at 60° C. for 5 h, then partitioned between 1N HCl and ether. The organic phase was washed with water and brine, dried over magnesium sulfate, filtered, and evaporated in vacuo. Purification by chromatography gave the desired product. $^1$H NMR (CDCl$_3$) δ 0.99 (m, 6H), 1.72 (m, 8H), 2.10 (m, 2H), 2.35 (m, 2H), 2.62 (t, 2H), 2.84 (t, 2H), 7.41 (s, 1 H).

The examples listed in Table I at the end of the Description were prepared using the same or similar protocols as described for the examples (1-8) listed above.

ALTERNATE SYNTHESES OF INTERMEDIATES AND EXAMPLES 1 AND 2

2,4-Dipropylresorcinol, Intermediate 1 (5,7-dipropyl-6-hydroxy-3-trifluoromethyl-1,2-benzisoxazole) and the compounds of Examples 1 and 2 and the methyl ester of Example 22 have been made by using the synthetic sequences shown below. In the overall sequence, 2,4-dipropylresorcinol is first synthesized using a different method than that described above, then the resulting 2,4-dipropylresorcinol is converted to 5,7-dipropyl-6-hydroxy-3-trifluoromethyl-1,2-benzisoxazole (Intermediate I), and Intermediate I is converted to the compounds provided in Examples 1 and 2 by improvements in the methods described in the examples above.

Synthesis of 2,4-Dipropylresorcinol

Step 1

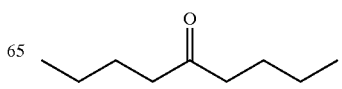

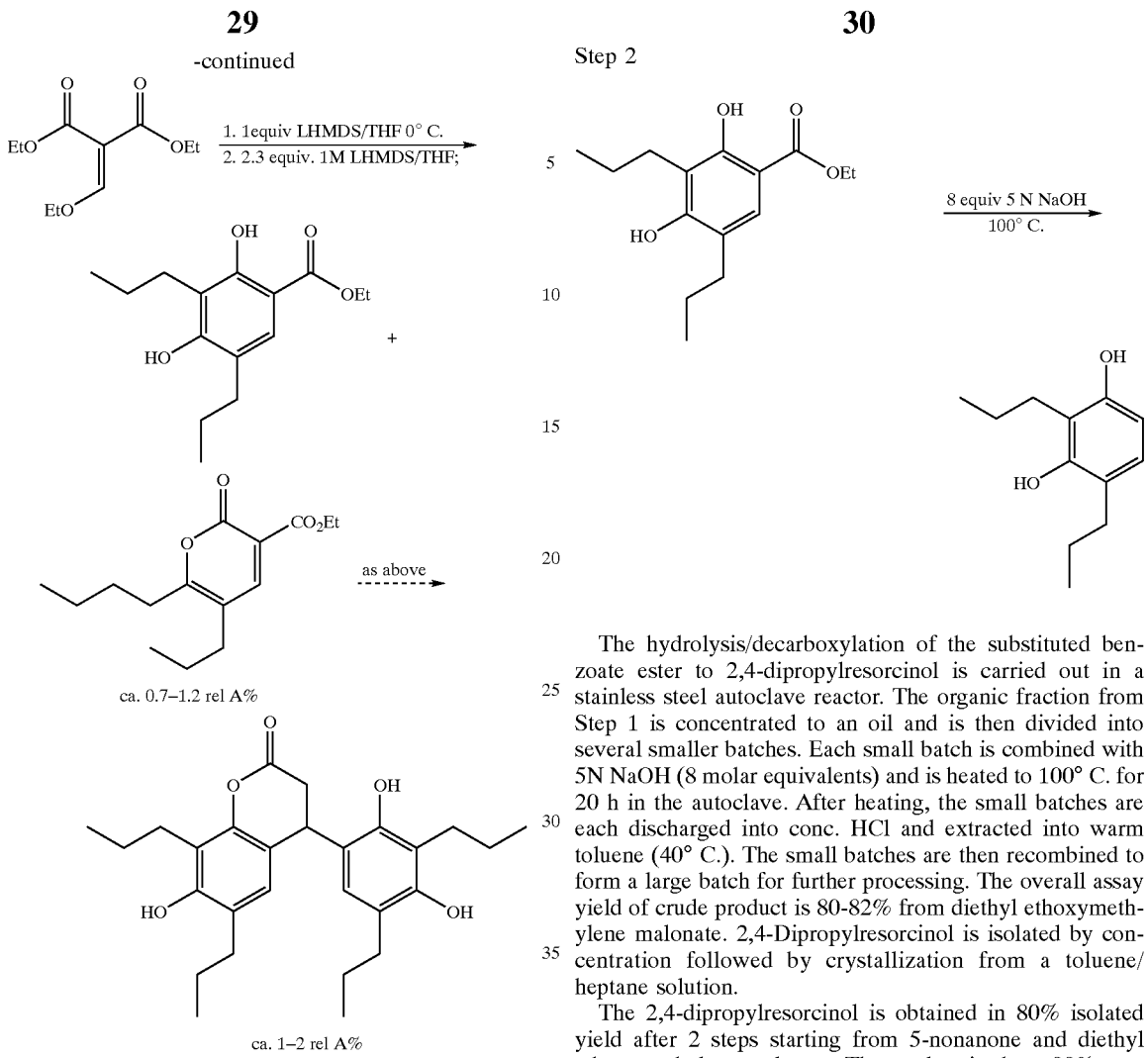

The sequence of reactions is carried out on a scale of about 50-55 moles, which is equivalent to about 7.1-7.8 kg of starting 5-nonanone. In the synthesis of 2,4-dipropylresorcinol, equimolar amounts of 5-nonanone and diethyl ethoxymethylene malonate (available from Aldrich) are condensed under strongly basic conditions. Excess lithium hexamethyldisilazide (LHMDS) in THF (3.3 equiv. total) is used. The excess strong base favors formation of the desired benzoate ester relative to the pyrone by-product (C vs. O condensation).

5-Nonanone is added to a solution of LHMDS/THF (1 eq.) at 0° C. After a few minutes, diethyl ethoxymethylene malonate (1 equiv) is added to the reaction mixture. The mixture is stirred briefly and is then added to an additional 2.3 equivalents of LHMDS/THF. After heating to 40° C. and aging for 4 h, HPLC analysis indicates an 80-82% assay yield of the ester (99.5% pure by LC with 0.5 relative area % pyrone). After pouring the product into 2N HCl and phase separating, the solvent is switched to heptane, from which the ester can be isolated as a crystalline solid. The crystallization step results in an 8% loss of product in the mother liquors at −35° C. The product does not need to be isolated, and the THF solution of product is preferably carried forward to the hydrolysis-decarboxylation step.

The hydrolysis/decarboxylation of the substituted benzoate ester to 2,4-dipropylresorcinol is carried out in a stainless steel autoclave reactor. The organic fraction from Step 1 is concentrated to an oil and is then divided into several smaller batches. Each small batch is combined with 5N NaOH (8 molar equivalents) and is heated to 100° C. for 20 h in the autoclave. After heating, the small batches are each discharged into conc. HCl and extracted into warm toluene (40° C.). The small batches are then recombined to form a large batch for further processing. The overall assay yield of crude product is 80-82% from diethyl ethoxymethylene malonate. 2,4-Dipropylresorcinol is isolated by concentration followed by crystallization from a toluene/heptane solution.

The 2,4-dipropylresorcinol is obtained in 80% isolated yield after 2 steps starting from 5-nonanone and diethyl ethoxymethylene malonate. The product is about 99% pure by LC assay. One large batch had a larger amount of the dimeric by-product shown in the drawing of the Step 1 sequence. In order to obtain 99% purity in that batch, a larger loss of 2,4-dipropylresorcinol product was necessary during crystallization, resulting in a 69% yield of 2,4-dipropylresorcinol after 2 steps.

Conversion of 2,4-Dipropylresorcinol to Intermediate I

Step 1

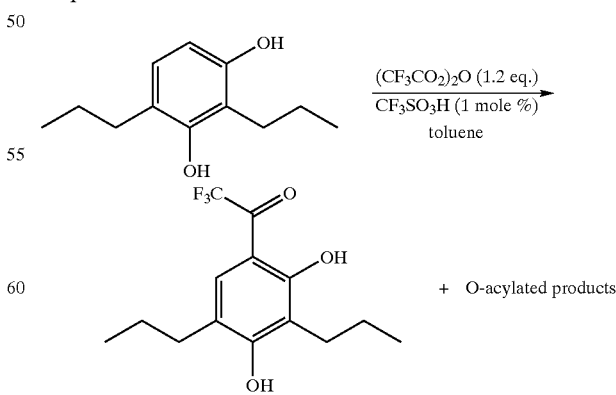

2,4-Dipropylresorcinol (about 8.5 kg) is mixed with 1 mole % of trifluoromethanesulfonic acid in toluene. Trifluoroacetic anhydride (TFAA, 2 eq.) is then added, and the mixture is allowed to react for 1-2 hours at ambient temperature. This results in complete conversion of the 2,4-dipropylresorcinol with greater than 90% assay yield of trifluoroacetophenone product. The reaction mixture is solvent switched to MTBE, washed with NaHCO₃ and brine, and concentrated to a crude solid for use in the next step.

Step 2

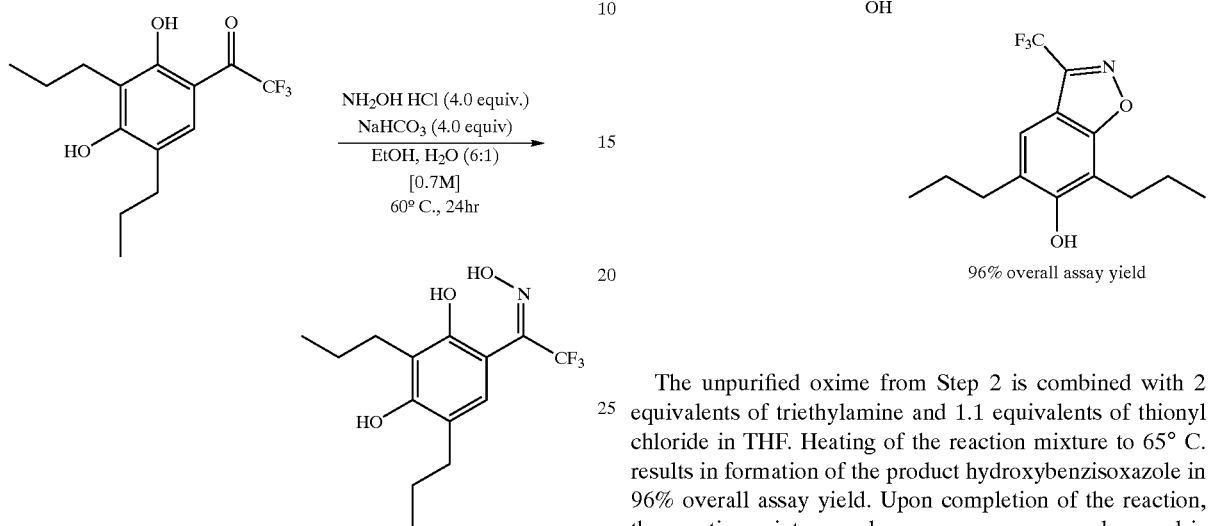

The crude solid trifluoroacetophenone from Step 1 (11.54 kg) is dissolved in 48 L of ethanol and is charged into a 100 L round-bottom flask. Water (8L) is then added. Hydroxylamine hydrochloride (NH₂OH.HCl, 11.05 kg) is added to the stirred mixture, followed by the addition of NaHCO₃ (13.36 kg). The heterogeneous solution is stirred at 60° C. overnight. The reaction is complete within 24 hours by LC assay. Work-up consists of the addition of 40L of water and 25L of toluene, followed by transfer to an extractor. The flask is rinsed with an additional 25L of toluene, which is also transferred to the extractor. The layers are separated, and the organic layer is extracted with one washing of 60L of 1N NaOH. The layers are separated, and the NaOH layer is neutralized with 12N HCL to pH=6.1. The aqueous layer is then extracted with 60L of toluene. The layers are separated and the aqueous layer is extracted a second time with toluene. The combined organic layers are washed with 4L of water. The organic layer is concentrated to a crude solid which can be used in the next step without further purification. Alternatively, the product can be crystallized from a toluene/heptane mixture. The product is predominantly the E oxime (shown in the equation above) rather than the Z oxime and is obtained in 85% yield from 2,4-dipropylresorcinol.

Step 3

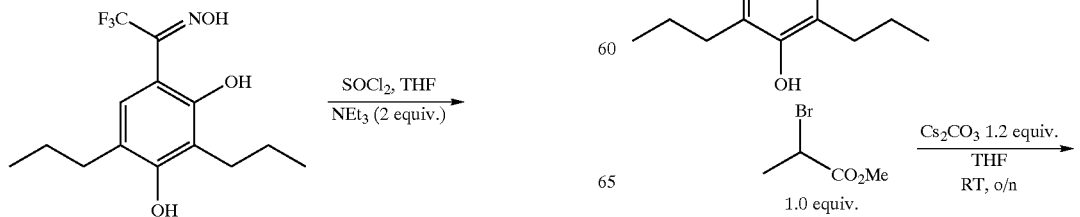

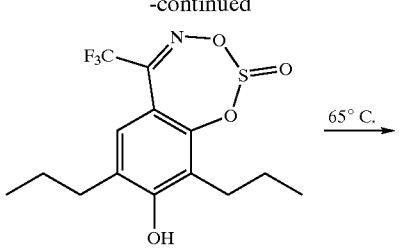

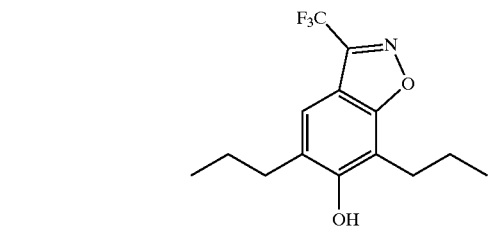

96% overall assay yield

The unpurified oxime from Step 2 is combined with 2 equivalents of triethylamine and 1.1 equivalents of thionyl chloride in THF. Heating of the reaction mixture to 65° C. results in formation of the product hydroxybenzisoxazole in 96% overall assay yield. Upon completion of the reaction, the reaction mixture undergoes an aqueous workup and is subsequently crystallized from aqueous isopropyl acetate (IPA).

The reaction proceeds through an intermediate which is not isolated but is converted in situ under the conditions of the reaction (65° C. temperature) to the hydroxybenzisoxazole product. The intermediate can be obtained cleanly at ambient temperature and has been identified by NMR and MS as the cyclic sulfite shown in the equation. The cyclic sulfite loses SO₂ when it is heated to 65° C.

Preparation of methyl 2-[(5,7-dipropyl-3-trifluoromethyl-1,2-benzisoxazol-6-yl)oxy]-2-methylpropionate (Example 1) and 2-[(5,7-dipropyl-3-trifluoromethyl-1,2-benzisoxazol-6-yl)oxy]-2-methylpropionic acid (Example 2)

Step 1. Methyl 2-[(5,7-dipropyl-3-trifluoromethyl-1,2-benzisoxazol-6-yl)oxy]propionate (Methyl ester of Example 22)

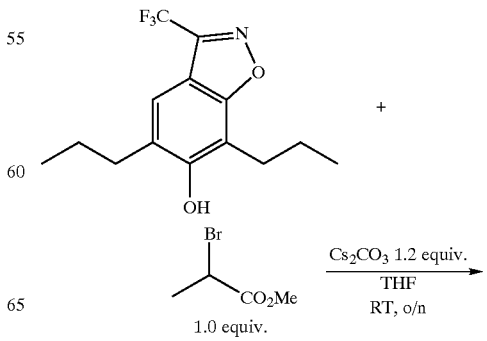

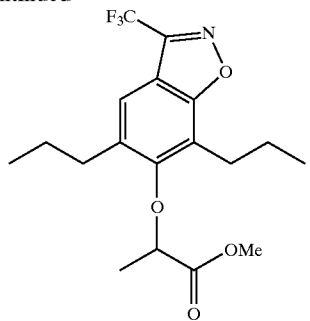

A 100 L round bottom flask equipped with overhead stirring, nitrogen inlet, and addition funnel is charged with 8.5 kg of 5,7-dipropyl-6-hydroxy-3-trifluoromethyl -1,2-benzisoxazole as a solid at room temperature. This is followed by the addition of 30L of THF and 12,051.3 g (1.2 eq.) of cesium carbonate. Methyl 2-bromopropionate (4,942 g, 1.0 eq.) is added to the heterogenous mixture. The reaction mixture is stirred under nitrogen at room temperature overnight. After the reaction is complete (about 12 hours), as determined by LC assay, 18 L of water is added to the reaction vessel. The mixture is diluted with 30 L of MTBE, and is transferred to a 100L extractor. After the phases are separated, the organic layer is washed with $H_2O$ (9L). The product is obtained in 98% assay yield.

Step 2. Methyl 2-[(5,7-dipropyl-3-trifluoromethyl-1,2-benzisoxazol-6-yl)oxy]-2-methylpropionate (Example 1)

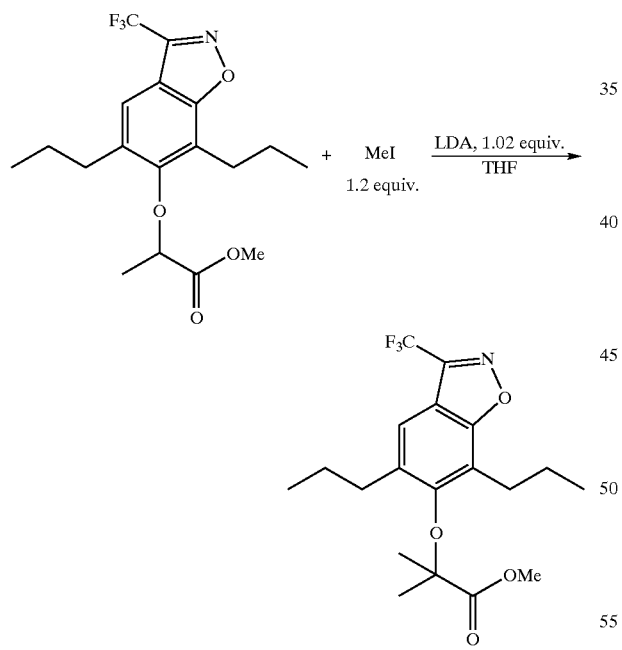

The solvent from Step 1 is switched to THF. A 100 L round bottom flask equipped with overhead stirring, nitrogen inlet, and addition funnel is charged with a solution of 10.5 kg of methyl 2-[(5,7-dipropyl-3-trifluoromethyl-1,2-benzisoxazol -6-yl)oxy] propionate in 37.5L of THF. The reaction vessel is cooled to −78° C. , and 1.02 equivalents of lithium diisopropylamide (LDA), which has been carefully measured, is slowly added to the reactor with stirring, maintaining the reaction temperature below −60° C. After the addition of LDA, the reaction is stirred at −78° degree for 15 min. MeI is added slowly, maintaining the reaction temperature below −40° C. The reaction is stirred at −78° C. degree for 15 min before warming gradually to −30° C. over a four hour period.

The reaction mixture is then quenched by pouring it into 12L of 15 wt % aqueous $NH_4Cl$ solution. 20L MTBE is used to rinse the reaction vessel and is mixed with the aqueous solution. After phase separation, assay of the organic phase by LC indicates a 94% yield of the desired product, with about 1.5% of the starting material (methyl 2-[(5,7-dipropyl-3-trifluoromethyl-1,2-benzisoxazol-6-yl)oxy]propionate from Step 1).

Step 3. Selective hydrolysis of methyl 2-[(5,7-dipropyl-3-trifluoromethyl-1,2-benisoxazol -6-yl)oxy] propionate

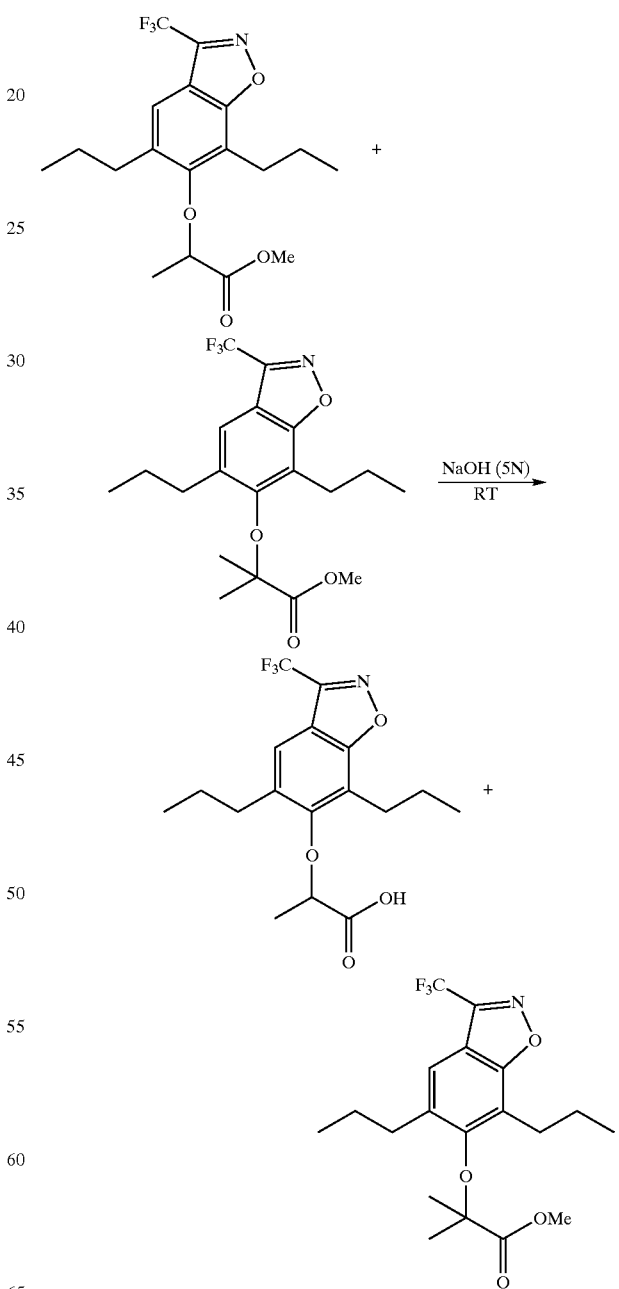

10L of NaOH (5N) is added to the organic phase from the previous step (MTBE solvent, no methanol), and the mixture is stirred at ambient temperature. The hydrolysis reaction is followed by LC. The non-methylated starting material from Step 2 (methyl 2-[(5,7-dipropyl-3-trifluoromethyl-1,2-benzisoxazol-6-yl)oxy]propionate) hydrolyzes much faster than the methylated product in aqueous NaOH if no methanol is present. When the area percent of non-methylated starting material from Step 2 decreases to below 0.8% as indicated by LC, the layers are separated. The organic layer is washed with H$_2$O twice (10L, 5L) to remove the acid from the hydrolysis of the non-methylated starting material. The organic layer is then assayed.

Step 4. 2-[(5,7-dipropyl-3-trifluoromethyl-1,2-benzisoxazol-6-yl)oxy]-2-methylpropionic acid

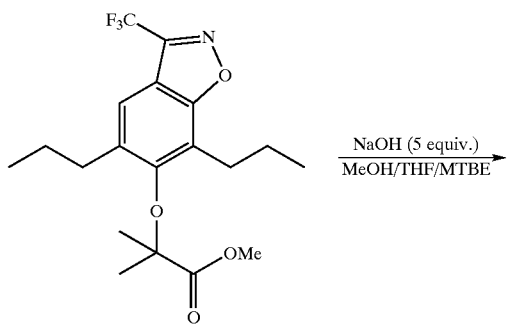

NaOH (5 equiv.)
MeOH/THF/MTBE

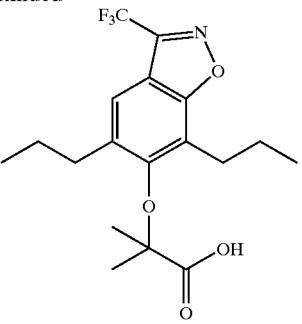

20L of aqueous NaOH (5N) and 8L MeOH are added to the organic layer from the previous step. The mixture is stirred at 48° C. overnight. When the reaction is complete as indicated by LC assay, the layers are separated. The organic fraction is extracted first with 30L of water and then a second time with 8L of water. The aqueous and organic fractions are both assayed to make sure that the desired product is all in the aqueous fractions. The aqueous fractions are combined and acidified with 12N HCl to pH=4.7 as indicated by pH paper, and the product is extracted with two washings of MTBE (26L, 20L). The product is crystallized by solvent switching to heptane and cooling first to ambient temperature overnight and then to about −19° C. The free acid made from the hydroxybenzisoxazole intermediate in this 4-step sequence is isolated in about 92% yield without isolation of any of the intermediates.

The above nine-step sequence produces the free acid in an isolated yield of about 50% from starting 5-nonanone.

Hydroxybenzisoxazole Intermediate I can be made into other compounds provided in this application in addition to Examples 1 and 2. It can be made into any of the compounds having Formula I in which R3 and R4 are propyl and R5 is trifluoromethyl.

TABLE I

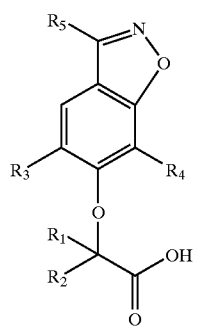

| Example | R1 | R2 | R3 | R4 | R5 | Partial $^1$H-Nmr Data (δ, ppm, CDCl$_3$) |
|---|---|---|---|---|---|---|
| 9 | methyl | methyl | Cl | propyl | trifluoromethyl | 1.67(s, 6H), 7.70(s, 1H) |
| 10 | ethyl | H | propyl | propyl | trifluoromethyl | 4.60(m, 1H), 7.44(s, 1H) |
| 11 | ethyl | methyl | propyl | propyl | trifluoromethyl | 1.15(t, 3H), 1.28(s, 3H), 7.43(s, 1H) |
| 12 | propyl | methyl | propyl | propyl | trifluoromethyl | 1.28(s, 3H), 1.47(m, 1H), 7.43(s, 1H) |
| 13 | propyl | H | propyl | propyl | trifluoromethyl | 4.64(t, 1H), 7.43(s, 1H) |
| 14 | propyl | propyl | propyl | propyl | trifluoromethyl | 0.85(t, 6H), 1.23(m, 2H), 7.42(s, 1H) |
| 15 | ethyl | ethyl | propyl | propyl | trifluoromethyl | 1.56–1.86(m, 4H), 7.41(s, 1H) |
| 16 | methyl | H | Cl | propyl | ethyl | 1.45(t, 3H), 1.64(d, 3H), 4.95(q, 1H), 7.55(s, 1H) |
| 17 | methyl | methyl | Cl | propyl | ethyl | 1.45(t, 3H), 2.97(q, 3H), 7.53(s, 1H) |
| 18 | methyl | H | Cl | propyl | trifluoromethyl | 1.67(d, 3H), 5.03(q, 1H), 7 72(s, 1H) |
| 19 | methyl | methyl | propyl | propyl | ethyl | 1.45(t, 3H), 3.00(q, 2H), 7.29(s, 1H) |
| 20 | methyl | methyl | propyl | propyl | methyl | 2.57(s, 3H), 7.27(s, 1H) |
| 21 | methyl | methyl | propyl | propyl | methoxy | 4.16(s, 3H), 7.28(s, 1H) |
| 22 | methyl | H | propyl | propyl | trifluoromethyl | 1.61(d, 3H), 4.71(q, 1H), 7.46(s, 1H) |
| 23 | methyl | H | propyl | propyl | phenyl | 1.61(d, 3H), 4.71(q, 1H), 7.57(s, 1H) |
| 24 | methyl | methyl | propyl | propyl | phenyl | 7.54(s, 1H), 7.58(m, 3H), 7.96(d, 2H) |

TABLE I-continued

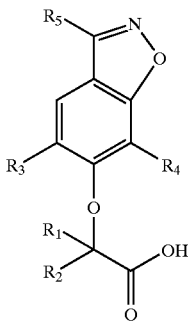

| Example | R1 | R2 | R3 | R4 | R5 | Partial $^1$H-Nmr Data ($\delta$, ppm, CDCl$_3$) |
|---|---|---|---|---|---|---|
| 25 | methyl | ethyl | propyl | propyl | phenyl | 1.16(t, 3H), 1.30(s, 3H), 7.54(s, 1H) |
| 26 | H | H | propyl | propyl | trifluoromethyl | 4.58(s, 2H), 7.47(s, 1H) |
| 27 | 4-penten-1-yl | H | propyl | propyl | trifuoromethyl | 4.62(m, 1H), 5.03(m, 2H), 5.80(m, 1H), 7.43(s, 1H) |
| 28 | cyclobutylidene | | propyl | propyl | trifuoromethyl | 2.37(m, 2H), 2.58(m, 2H), 7.50(s, 1H) |
| 29 | cyclohexylidene | | propyl | propyl | trifuoromethyl | 1.20(m, 1H), 2.30(d, broad, 2H), 7.40(s, 1H) |

What is claimed is:

1. A compound having the formula I:

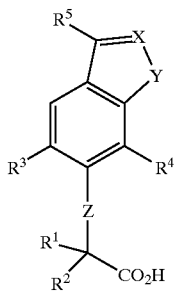

I and pharmaceutically acceptable salts thereof, wherein
- $R^1$ and $R^2$ are each independently selected from the group consisting of H, F, $C_{1-5}$ alkyl, $C_{2-5}$ alkenyl, and $C_{2-5}$ alkynyl, wherein said alkyl, alkenyl, and alkynyl may be linear or branched and are optionally substituted with 1–3 halogen atoms; or optionally $R^1$ and $R^2$ together form a $C_{3-6}$ cycloalkyl;
- $R^3$ and $R^4$ are each independently selected from the group consisting of $C_1$–$C_5$ alkyl, $C_{2-5}$ alkenyl, and $C_{2-5}$ alkynyl, wherein said alkyl, alkenyl, and alkynyl groups may be linear or branched and are optionally substituted with 1–5 fluorine atoms;
- X is N;
- Y is O or S;
- Z is O or S; and
- $R^5$ is selected from the group consisting of H, $C_{1-6}$ alkyl, $C_{2-6}$ alkenyl, $C_{2-6}$ alkynyl, $C_{6-10}$ Aryl, —O$C_{1-6}$ alkyl, —O$C_{2-6}$ alkenyl, —O$C_{2-6}$ alkynyl, —O$C_{6-10}$ Aryl, $C_{3-6}$ Cycloalkyl, 5-6-membered Heterocyclyl, 5-6-membered Heteroaryl, —O$C_{3-6}$ Cycloalkyl, —O 5-6-membered Heterocyclyl, —O 5-6 membered Heteroaryl, and a $C_{1-4}$ alkyl group which comprises at a position interrupting the chain or at the end of the chain a group selected from $C_{6-10}$ Aryl, $C_{3-6}$ Cycloalkyl, 5-6-membered Heterocyclyl, and 5-6-membered Heteroaryl, wherein each of said alkyl, alkenyl, alkynyl, -Oalkyl, -Oalkenyl, and -Oalkynyl is linear or branched and optionally substituted with 1–5 fluorine atoms and/or one —OCH$_3$ or —OCF$_3$ group, and each of said Aryl, Cycloalkyl, Heteroaryl, Heterocyclyl, —OAryl, —OCycloalkyl, -OHeteroaryl, and -OHeterocyclyl groups is optionally substituted with 1–7 halogen atoms and/or one —OCH$_3$ or —OCF$_3$ group.

2. A compound having the formula I as recited in claim 1, wherein Y is O.

3. A compound having the formula I as recited in claim 1, wherein Y is S.

4. A compound having formula I as recited in claim 1, wherein
- $R^5$ is selected from the group consisting of H, $C_{1-5}$ alkyl, $C_{2-5}$ alkenyl, $C_{2-5}$ alkynyl, O$C_{1-5}$ alkyl, O$C_{2-5}$ alkenyl, O$C_{2-5}$ alkynyl, and phenyl, wherein said alkyl, alkenyl, alkynyl, —Oalkyl, —Oalkenyl, and —Oalkynyl are optionally substituted with 1-5 fluorine atoms, and said phenyl is optionally substituted with 1-5 halogens.

5. A compound as recited in claim 1, wherein
- $R^1$ and $R^2$ are each H or $C_{1-3}$ alkyl, where the number of carbon atoms in $R^1$ and $R^2$ together is 0-5;
- $R^3$ and $R^4$ are each independently $C_{1-5}$ alkyl;
- $R^5$ is selected from the group consisting of $C_{1-5}$ alkyl and —O$C_{1-5}$ alkyl, wherein said alkyl and —Oalkyl are optionally substituted with 1-5 fluorine atoms, and
- Z is O.

6. A compound as recited in claim 5, wherein $R_5$ is $C_{1-3}$ alkyl, —O$C_{1-3}$ alkyl, CF$_3$, $C_2F_5$, —OCF$_3$ or —O$C_2F_5$; and $R^3$ and $R^4$ are each n-propyl.

7. A prodrug having Formula Ia,

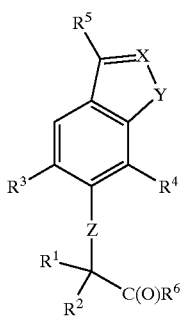

Ia and pharmaceutically acceptable salts thereof, wherein

39

R¹ and R² are each independently selected from the group consisting of H, F, $C_{1-5}$ alkyl, $C_{2-5}$ alkenyl, and $C_{2-5}$ alkynyl, wherein said alkyl, alkenyl, and alkynyl may be linear or branched and are optionally substituted with 1–3 halogen atoms; or optionally R¹ and R² together form a $C_{3-6}$ cycloalkyl;

R³ and R⁴ are each independently selected from the group consisting of $C_1$–$C_5$ alkyl, $C_{2-5}$ alkenyl, and $C_{2-5}$ alkynyl, wherein said alkyl, alkenyl, and alkynyl groups may be linear or branched and are optionally substituted with 1–5 fluorine atoms;

X is N;

Y is O or S;

Z is O or S;

R⁵ is selected from the group consisting of H, $C_{1-6}$ alkyl, $C_{2-6}$ alkenyl, $C_{2-6}$ alkynyl, $C_{6-10}$ Aryl, —$OC_{1-6}$ alkyl, —$OC_{2-6}$ alkenyl, —$OC_{2-6}$ alkynyl, —$OC_{6-10}$ Aryl, $C_{3-6}$ Cycloalkyl, 5-6-membered Heterocyclyl, 5-6-membered Heteroaryl, —$OC_{3-6}$ Cycloalkyl, —O 5-6-membered Heterocyclyl, —O 5-6 membered Heteroaryl, and a $C_{1-4}$ alkyl group which comprises at a position interrupting the chain or at the end of the chain a group selected from $C_{6-10}$ Aryl, $C_{3-6}$ Cycloalkyl, 5-6-membered Heterocyclyl, and 5-6-membered Heteroaryl, wherein each of said alkyl, alkenyl, alkynyl, -Oalkyl, -Oalkenyl, and -Oalkynyl is optionally substituted with 1-5 fluorine atoms and/or one —$OCH_3$ or —$OCF_3$ group, and each of said Aryl, Cycloalkyl, Heteroaryl, Heterocyclyl, —OAryl, —OCycloalkyl, —OHeteroaryl, and —OHeterocyclyl groups is optionally substituted with 1-7 halogen atoms and/or one —$OCH_3$ or —$OCF_3$ group;

R⁶ is selected from the group consisting of —OR⁷, —$OCH_2OR^7$, —$OCH(CH_3)OR^7$, —$OCH_2OC(O)R^7$, —$OCH(CH_3)OC(O)R^7$, —$OCH_2OC(O)OR^7$, —$OCH(CH_3)OC(O)OR^7$, —NR⁸R⁸ and —ONR⁸R⁸;

Each R⁷ is independently selected from $C_{1-6}$ alkyl optionally substituted with one or two groups selected from —$CO_2H$, —$CONH_2$, —$NH_2$, —OH, —OAc, NHAc, and phenyl; and Each R⁸ is independently selected from H and R⁷.

8. A compound selected from any of the structures of Examples 1-29, consisting of:

Example 1

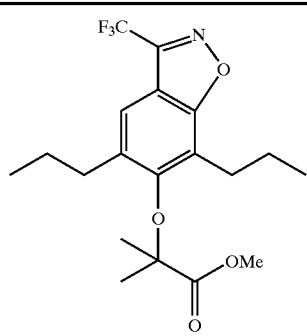

Example 2

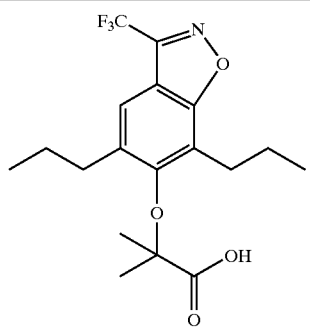

Example 3

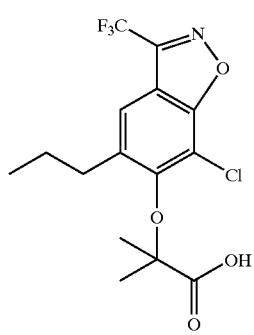

Example 4

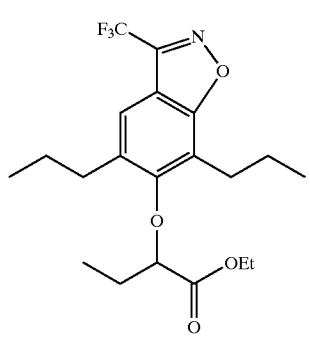

Example 5

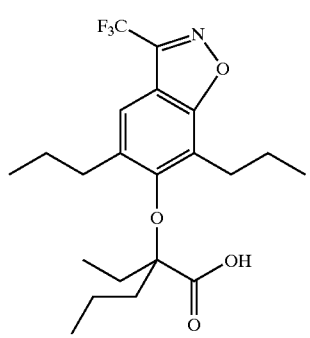

Example 6 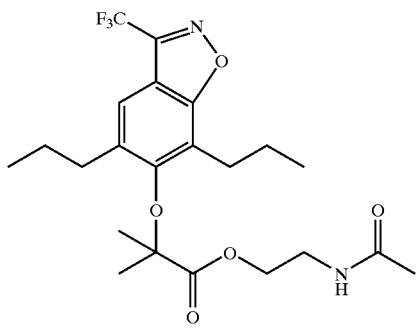

Example 7 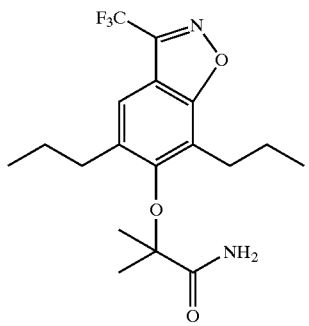

Example 8 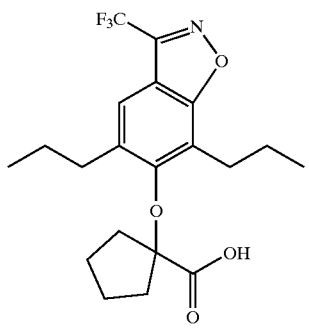

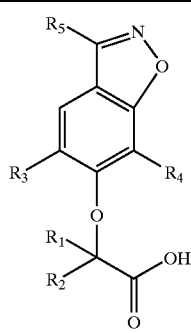

| Example | R1 | R2 | R3 | R4 | R5 |
|---|---|---|---|---|---|
| 9 | methyl | methyl | Cl | propyl | trifluoromethyl |
| 10 | ethyl | H | propyl | propyl | trifuoromethyl |
| 11 | ethyl | methyl | propyl | propyl | trifluoromethyl |
| 12 | propyl | methyl | propyl | propyl | trifluoromethyl |
| 13 | propyl | H | propyl | propyl | trifluoromethyl |
| 14 | propyl | propyl | propyl | propyl | trifluoromethyl |
| 15 | ethyl | ethyl | propyl | propyl | trifluoromethyl |
| 16 | methyl | H | Cl | propyl | ethyl |
| 17 | methyl | methyl | Cl | propyl | ethyl |
| 18 | methyl | H | Cl | propyl | trifluoromethyl |
| 19 | methyl | methyl | propyl | propyl | ethyl |
| 20 | methyl | methyl | propyl | propyl | methyl |
| 21 | methyl | methyl | propyl | propyl | methoxy |
| 22 | methyl | H | propyl | propyl | trifuoromethyl |
| 23 | methyl | H | propyl | propyl | phenyl |
| 24 | methyl | methyl | propyl | propyl | phenyl |
| 25 | methyl | ethyl | propyl | propyl | phenyl |
| 26 | H | H | propyl | propyl | trifuoromethyl |
| 27 | 4-penten-1-yl | H | propyl | propyl | trifuoromethyl |
| 28 | cyclobutylidene | | propyl | propyl | trifuoromethyl or |
| 29 | cyclohexylidene | | propyl | propyl | trifuoromethyl. |

9. A pharmaceutical composition comprising a compound of claim 1 and a pharmaceutically acceptable carrier.

10. A pharmaceutical composition comprising a compound of claim 7 and a pharmaceutically acceptable carrier.

11. A method for treating or controlling non-insulin dependent (Type 2) diabetes mellitus in a mammalian patient in need of such treatment which comprises administering to said patient a therapeutically effective amount of a compound of claim 1.

12. A method for treating or controlling hyperglycemia in a mammalian patient in need of such treatment which comprises administering to said patient a therapeutically effective amount of a compound of claim 1.

13. A method for treating or controlling lipid disorders, hyperlipidemia, or low HDL in a mammalian patient in need of such treatment which comprises administering to said patient a therapeutically effective amount of a compound of claim 1.

14. A method for treating or controlling obesity in a mammalian patient in need of such treatment which comprises administering to said patient a therapeutically effective amount of a compound of claim 1.

15. A method for treating or controlling hypercholesterolemia in a mammalian patient in need of such treatment which comprises administering to said patient a therapeutically effective amount of a compound of claim 1.

16. A method for treating or controlling hypertriglyceridemia in a mammalian patient in need of such treatment which comprises administering to said patient a therapeutically effective amount of a compound of claim 1.

17. A method for treating or controlling dyslipidemia and/or low HDL cholesterol in a mammalian patient in need of such treatment which comprises administering to said patient a therapeutically effective amount of a compound of claim 1.

18. A method for treating or controlling atherosclerosis in a mammalian patient in need of such treatment which comprises administering to said patient a therapeutically effective amount of a compound of claim 1.

19. A method of treating or controlling one or more diseases, disorders, or conditions selected from the group consisting of (1) non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) high blood pressure, (30) Syndrome X, (31) ovarian hyperandrogenism (polycystic ovarian syndrome), and other disorders where insulin resistance is a component, said method comprising the administration of an effective amount of a compound of claim 1.

20. A method of treating or controlling one or more diseases, disorders, or conditions selected from the group consisting of (1) diabetes mellitus, and especially non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) high blood pressure, (30) Syndrome X, (31) ovarian hyperandrogenism (polycystic ovarian syndrome), and other disorders where insulin resistance is a component, said method comprising the administration of an effective amount of a compound of claim 1, and an effective amount of one or more other compounds selected from the group consisting of:

(a) insulin sensitizers selected from the group consisting of (i) PPARγ agonists; (ii) biguanides; (iii) protein tyrosine phosphatase-1B (PTP-1B) inhibitors, and (iv) dipeptidyl peptidase IV (DP-IV) inhibitors;

(b) insulin or insulin mimetics;

(c) sulfonylureas;

(d) a-glucosidase inhibitors;

(e) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA :cholesterol acyltransferase inhibitors, and (viii) anti-oxidants;

(f) PPARδ agonists;

(g) antiobesity compounds;

(h) an ileal bile acid transporter inhibitor; and (i) agents intended for use in inflammatory conditions.

21. A method for the treatment or control of one or more conditions selected from hypercholesterolemia, atherosclerosis, low HDL levels, high LDL levels, hyperlipidemia, hypertriglyceridemia, and dyslipidemia, which method comprises administering to a mammalian patient in need of such treatment a therapeutically effective amount of a compound as recited in claim 1.

22. The method as recited in claim 21, wherein the compound of claim 1 is administered with an HMG-CoA reductase inhibitor.

23. The method as recited in claim 22, wherein the HMG-CoA reductase inhibitor is a statin.

24. The method as recited in claim 23, wherein the statin is selected from the group consisting of lovastatin, simvastatin, pravastatin, fluvastatin, atorvastatin, itavastatin, ZD-4522 and rivastatin.

25. A method for the treatment or control of one or more conditions selected from inflammatory conditions, inflammatory bowel disease, Crohn's disease, and ulcerative colitis, which method comprises administering to a mammalian patient in need of such treatment a therapeutically effective amount of a compound as recited in claim 1.

26. The method as recited in claim 25, wherein the compound according to claim 1 is administered with an HMG-CoA reductase inhibitor.

27. The method as recited in claim 26, wherein the HMG-CoA reductase inhibitor is a statin selected from the group consisting of lovastatin, simvastatin, pravastatin, fluvastatin, atorvastatin, itavastatin, ZD-4522 and rivastatin.

28. A method for treating or controlling atherosclerosis in a mammalian patient in need of such treatment comprising the administration to said patient of an effective amount of a compound of claim 1 and an effective amount of an HMG-CoA reductase inhibitor.

29. A pharmaceutical composition for the treatment or control of atherosclerosis, comprising: (1) a compound according to claim 1, (2) an HMG-CoA reductase inhibitor, and (3) a pharmaceutically acceptable carrier.

30. A pharmaceutical composition comprising (1) a compound according to claim 1, (2) one or more compounds selected from the group consisting of:

(a) insulin sensitizers selected from the group consisting of (i) PPARγ agonists (ii) biguanides; (iii) protein tyrosine phosphatase-1B (PTP-1B) inhibitors, and (iv) dipeptidyl peptidase IV (DP-IV) inhibitors;

(b) insulin or insulin mimetics;

(c) sulfonylureas;

(d) u-glucosidase inhibitors;

(e) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption (vii) acyl CoA:cholesterol acyltransferase inhibitors, and (viii) anti-oxidants;

(f) PPAR6 agonists;

(g) antiobesity compounds;

(h) an heal bile acid transporter inhibitor; and (i) agents intended for use in inflammatory conditions; and (3) a pharmaceutically acceptable carrier.

31. A compound as recited in claim 1 wherein $R^3$ and $R^4$ are each independently $C_{1-5}$ alkyl.

* * * * *